United States Patent
Uemura et al.

(10) Patent No.: US 11,837,323 B2
(45) Date of Patent: Dec. 5, 2023

(54) DEVICE AND METHOD FOR SEARCHING COMPOUND

(71) Applicant: FUJITSU LIMITED, Kawasaki (JP)

(72) Inventors: Taiki Uemura, Kawasaki (JP); Takayuki Shibasaki, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 909 days.

(21) Appl. No.: 16/534,650

(22) Filed: Aug. 7, 2019

(65) Prior Publication Data

US 2020/0082904 A1 Mar. 12, 2020

(30) Foreign Application Priority Data

Sep. 11, 2018 (JP) .................................. 2018-169832

(51) Int. Cl.
*G01N 33/48* (2006.01)
*G16B 5/00* (2019.01)
*G16B 50/00* (2019.01)

(52) U.S. Cl.
CPC .............. *G16B 5/00* (2019.02); *G16B 50/00* (2019.02)

(58) Field of Classification Search
None
See application file for complete search history.

(56) References Cited

U.S. PATENT DOCUMENTS

2003/0130797 A1   7/2003   Skolnick et al.

FOREIGN PATENT DOCUMENTS

| JP | 2002-536301 | 10/2002 |
|---|---|---|
| JP | 2008-146529 | 6/2008 |

OTHER PUBLICATIONS

Li, Ying Wai, Thomas Wüst, and David P. Landau. "Monte Carlo simulations of the HP model (the "Ising model" of protein folding)." Computer physics communications 182.9 (2011): 1896-1899.*
Cipra, Barry A. "An introduction to the Ising model." The American Mathematical Monthly 94.10 (1987): 937-959.*
Huang, Kerson. Statistical mechanics. John Wiley & Sons, 1987.*
R. Babbush et.al., "Construction of Energy Functions for Lattice Heteropolymer Models: A Case Study in Constraint Satisfaction Programming and Adiabatic Quantum Optimization" arXiv:quant-ph/1211.3422v2 (https://arxiv.org/abs/1211.3422) Jun. 13, 2013.
Office Action dated Mar. 13, 2023 for Chinese Application No. 201910783431.2, 16pp.

* cited by examiner

*Primary Examiner* — Anna Skibinsky
(74) *Attorney, Agent, or Firm* — STAAS & HALSEY LLP

(57) ABSTRACT

A device including: defining unit to define lattice space that is collection of lattices compound groups are sequentially arranged; limiting unit to, in the case where any of the compound groups is arranged in any of the lattices of lattice space followed by arranging next compound group in the lattice space, generate limited lattice space created by eliminating, from the lattice space, undesirable regions for the next compound group to be arranged; and assigning unit to assign bit to each of lattice points, to which the compound groups can be arranged, in the limited lattice space; and an arithmetic unit configured to perform ground state search on Ising model obtained through conversion based on restriction conditions related to each lattice point according to simulated annealing, to calculate minimum energy of the Ising model, wherein the device is for searching compound in which the compound groups are linked with one another.

7 Claims, 22 Drawing Sheets

FIG. 14A
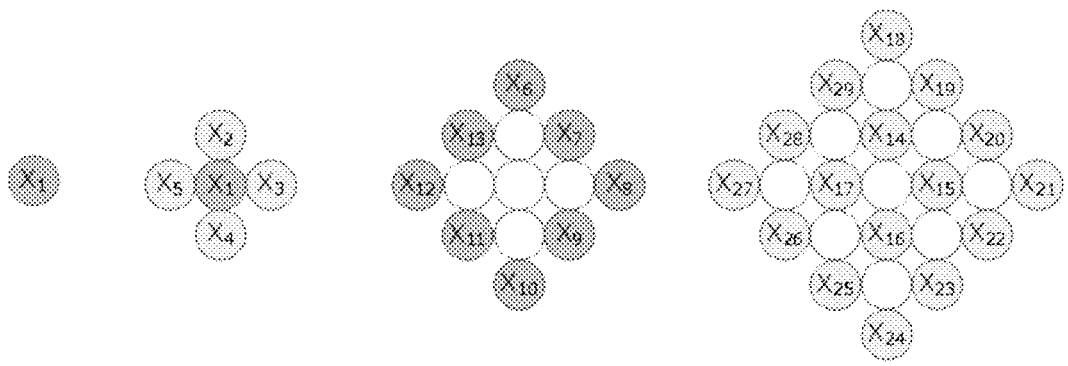
FIG. 14B
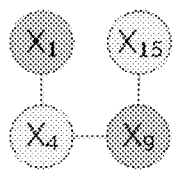
FIG. 15
|    | $X_1$ | $X_2$ | $X_3$ |
|----|-------|-------|-------|
| $X_1$ |   | 2 | 0 |
| $X_2$ | 2 |   | 4 |
| $X_3$ | 0 | 4 |   |

DEVICE AND METHOD FOR SEARCHING COMPOUND

CROSS-REFERENCE TO RELATED APPLICATION

This application is based upon and claims the benefit of priority of the prior Japanese Patent Application No. 2018-169832, filed on Sep. 11, 2018, the entire contents of which are incorporated herein by reference.

FIELD

The embodiments discussed herein relate to a method and device for searching a compound.

BACKGROUND

A protein is a chain polymer where amino acids are linked one-dimensionally without branching. A protein forms a certain conformation (three-dimensional shape) by folding a chain polymer thereof. A conformation of a protein is determined by a sequence of amino acids.

A conformation of a protein is deeply related to functions of a protein. A molecule-recognition function of a protein is expressed by specifically bounding a certain region within a conformation thereof to a certain molecule. Therefore, it is important to determine a conformation of a protein to understand functions of the protein.

For example, a conformation of a protein can be determined by X-ray crystallography, or nuclear magnetic resonance spectroscopy (NMR). However, it takes a long time to determine a conformation of one protein by X-ray crystallography or NMR. According to X-ray crystallography, moreover, a single crystal of one kind of protein is created first. When the single crystal cannot be created, X-ray crystallography cannot be performed on a conformation of the protein. Moreover, NMR can determine a conformation of a protein in an aqueous solution without crystallizing the protein, but a large quantity of information related to a conformation of the protein cannot be obtained when the protein is a large protein.

Meanwhile, a sequence of amino acids of a protein can be relatively easily determined from genetic information or the protein itself, even when a conformation of the protein is unknown.

Accordingly, there have been attempts to predict a conformation of a protein from a sequence of amino acids. For example, there is a method for determining folding of a protein according to the diamond encoding method. The method is a method for embedding positions of chain amino acids in a diamond lattice, and can express a three-dimensional structure (conformation). Energy of the conformation determined by the above-described method can be calculated, for example, using the Ising model. To solve the Ising model, for example, an annealing machine is used. One example of the background technology is disclosed in R. Babbush et. al., Construction of Energy Functions for Lattice Heteropolymer Models: A Case Study in Constraint Satisfaction Programming and Adiabatic Quantum Optimization, arXiv:quant-ph/1211.3422v2 (https://arxiv.org/abs/1211.3422).

SUMMARY

According to one aspect of the present disclosure, a device for searching a compound includes: a defining unit configured to define a lattice space that is a collection of lattices where a plurality of compound groups are sequentially arranged; a limiting unit configured to, in the case where any of the compound groups is arranged in any of the lattices of the lattice space, followed by arranging a next compound group in the lattice space, generate a limited lattice space that is a space created by eliminating, from the lattice space, undesirable regions for the next compound group to be arranged; an assigning unit configured to assign a bit to each of lattice points, to which the compound groups can be arranged, in the limited lattice space; and an arithmetic unit configured to perform a ground state search on an Ising model obtained through conversion based on restriction conditions related to each of the lattice points according to simulated annealing, to thereby calculate minimum energy of the Ising model. The device is a device for searching a compound, in which a plurality of compound groups are linked with one another.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 14A is a view for describing $H_{pair}$ (part 1);

FIG. 14B is a view for describing $H_{pair}$ (part 2).

FIG. 15 is a view illustrating one example of a weight file;

DESCRIPTION OF EMBODIMENTS

Figure 1:
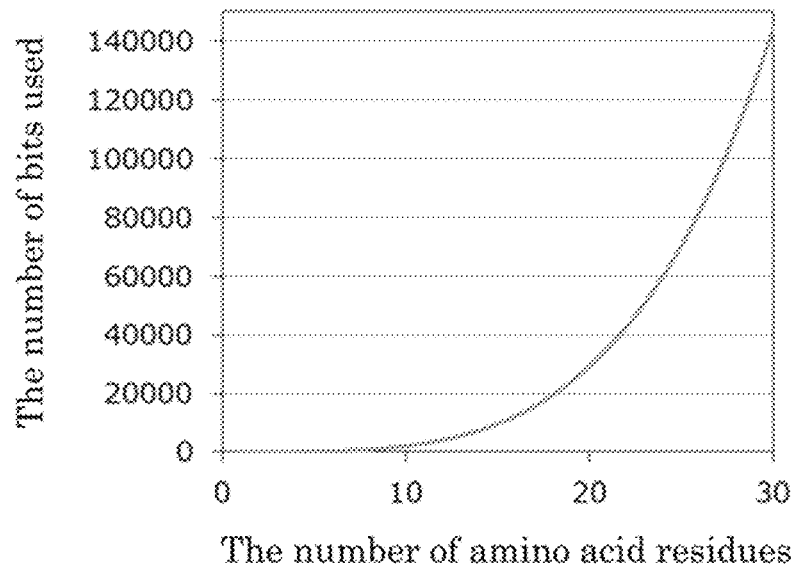
FIG. 1 is a graph depicting a relationship between the number of amino acid residues and the number of bits used.

The disclosed device for searching a compound is a compound search device for searching a compound in which a plurality of compound groups are linked with one another.

The device for searching a compound includes at least a defining unit, a limiting unit, an assigning unit, and an arithmetic unit.

The defining unit is configured to define a lattice space that is a collection of lattices where a plurality of compound groups are sequentially arranged.

The limiting unit is configured to, in the case where any of the compound groups is arranged in any of the lattices of the lattice space, followed by arranging a next compound group in the lattice space, generate a limited lattice space that is a space created by eliminating, from the lattice space, undesirable regions for the next compound group to be arranged.

The assigning unit is configured to assign a bit to each of lattice points, to which the compound groups can be arranged, in the limited lattice space.

The arithmetic unit is configured to perform a ground state search on an Ising model obtained through conversion based on restriction conditions related to each of the lattice points according to simulated annealing, to thereby calculate minimum energy of the Ising model.

The disclosed method for searching a compound is a method for searching a compound in which a plurality of compound groups are linked with one another.

The method for searching a compound allows a computer to perform a method including: defining a lattice space that is a collection of lattices where a plurality of compound groups are sequentially arranged; in the case where any of the compound groups is arranged in any of the lattices of the lattice space, followed by arranging a next compound group in the lattice space, generating a limited lattice space that is a space created by eliminating, from the lattice space, undesirable regions for the next compound group to be arranged; assigning a bit to each of lattice points, to which the compound groups can be arranged, in the limited lattice space; and performing a ground state search on an Ising model obtained through conversion based on restriction conditions related to each of the lattice points according to simulated annealing, to thereby calculate minimum energy of the Ising model.

The disclosed program for searching a compound is a program for causing a computer to execute a method for searching a compound in which a plurality of compound groups are linked with one another.

The method includes: defining a lattice space that is a collection of lattices where a plurality of compound groups are sequentially arranged; in the case where any of the compound groups is arranged in any of the lattices of the lattice space, followed by arranging a next compound group in the lattice space, generating a limited lattice space that is a space created by eliminating, from the lattice space, undesirable regions for the next compound group to be arranged; assigning a bit to each of lattice points, to which the compound groups can be arranged, in the limited lattice space; and performing a ground state search on an Ising model obtained through conversion based on restriction conditions related to each of the lattice points according to simulated annealing, to thereby calculate minimum energy of the Ising model.

Since there is a restriction in hardware of an anealing machine for solving an Ising model, there are restrictions in the number of arithmetic bits or quantum bits the annealing machine can handle.

Meanwhile, the number of bits used for solving a problem of folding of a protein increases exponentially relative to a scale of the protein (the number of amino acid residues) as demonstrated in the graph of FIG. 1.

As described above, a scale of a problem to be solved is limited by the restriction in the number of bits handled by hardware, and therefore search targets of amino acids cannot be expanded.

The present disclosure aims to provide a device, method, and program for searching a program that can suppress the number of arithmetic bits or quantum bits used for a search of a predetermined compound to enable to search a compound having a large molecular weight.

One aspect of the present disclosure can provide a device for searching a program that can suppress the number of arithmetic bits or quantum bits used for a search of a predetermined compound to enable to search a compound having a large molecular weight.

Moreover, one aspect of the present disclosure can provide a method for searching a program that can suppress the number of arithmetic bits or quantum bits used for a search of a predetermined compound to enable to search a compound having a large molecular weight.

Furthermore, one aspect of the present disclosure can provide a program for searching a program that can suppress the number of arithmetic bits or quantum bits used for a search of a predetermined compound to enable to search a compound having a large molecular weight.

Before describing the details of the disclosed technology, a method for determining folding of a protein that is a compound according to the diamond encoding method will be described.

A search of a stable conformation of a protein is typically performed in the following manner.

Figure 2A:
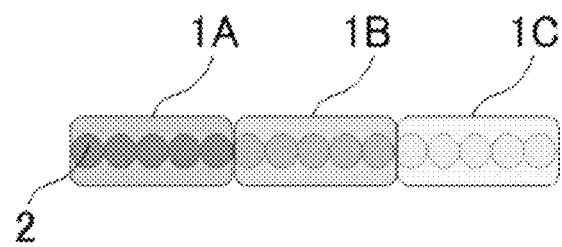
FIG. 2A is a schematic view for searching a stable conformation of a protein (part 1)

First, coarse graining of a protein is performed (FIG. 2A). For example, the coarse graining of a protein is performed by coarse graining atoms 2 constituting the proteins into amino acid residue units 1A, 1B, and 1C.

Figure 2B:
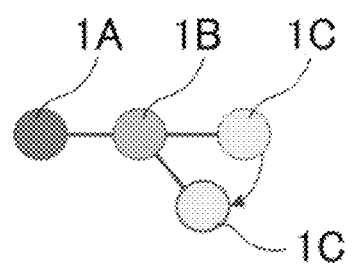
FIG. 2B is a schematic view for searching the stable conformation of the protein (part 2)

Next, a structure search is performed using the created coarse-grained model (FIG. 2B). The structure search is performed according to the diamond encoding method described later.

Figure 2C:
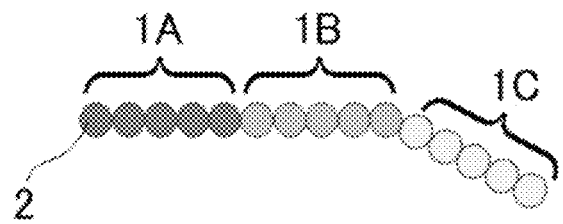
FIG. 2C is a schematic view for searching the stable conformation of the protein (part 3)

Next, the coarse-grained model is returned back to the whole atoms (FIG. 2C).

The diamond encoding method is a method where a linear amino acid is embedded in a position on a diamond lattice, and can represents a three-dimensional structure. For the sake of simplicity, a two-dimensional structure is described as an example.

Figure 3A:
FIG. 3A is a schematic view for describing the diamond encoding method (part 1)

Used as an example is a linear pentapeptide having a structure illustrated in FIG. 3A, where 5 amino acid residues are linked, when the structure is represented by a linear structure. In FIGS. 3A to 3E, a number in each circle is a number of the amino acid residue in the linear pentapeptide.

Figure 3B:
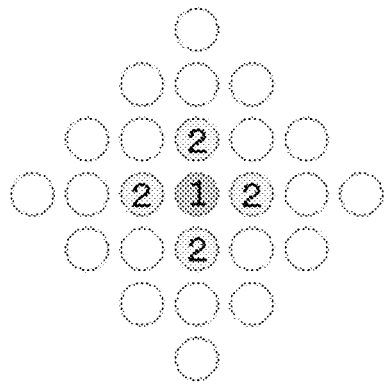
FIG. 3B is a schematic view for describing the diamond encoding method (part 2)

First, an amino acid residue of No. 1 is arranged at a center of a diamond lattice as illustrated in FIG. 3A, positions where an amino acid residue of No. 2 can be arranged are limited to positions next to the center as illustrated in FIG. 3B (the positions numbered as 2).

Figure 3C:
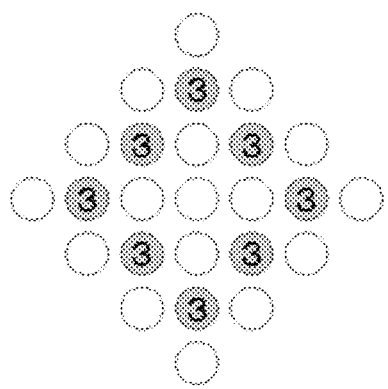
FIG. 3C is a schematic view for describing the diamond encoding method (part 3)

Next, in FIG. 3C, positions to which an amino acid residue of No. 3 bonded to next to the amino acid residues of No. 2 can be arranged are limited to positions next to the positions numbered as 2 (the positions numbered as 3) in FIG. 3B.

Figure 3D:
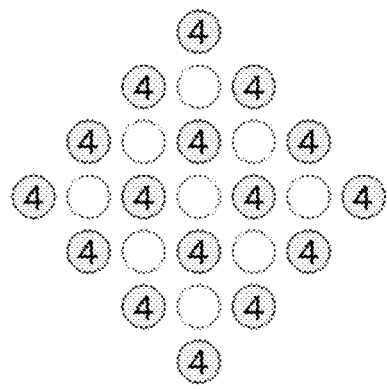
FIG. 3D is a schematic view for describing the diamond encoding method (part 4)

Next, in FIG. 3D, positions to which an amino acid residue of No. 4 bonded to next to the amino acid residues of No. 3 can be arranged are limited to positions next to the positions numbered as 3 (the positions numbered as 4) in FIG. 3C.

Figure 3E:
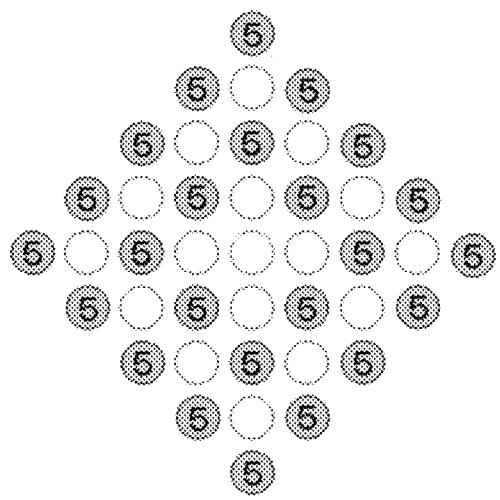
FIG. 3E is a schematic view for describing the diamond encoding method (part 5)

Next, in FIG. 3E, positions to which an amino acid residue of No. 5 bonded to next to the amino acid residues of No. 4 can be arranged are limited to positions next to the positions numbered as 4 (the positions numbered as 5) in FIG. 3D.

In the manner as described above, a three-dimensional structure can be expressed by linking the positions where amino acid residues can be arranged.

As amino acid residues are bounded into a straight chain, a radius (n) of a diamond lattice space is set according to the number (n) of amino acid residues to be bounded.

However, amino acid residues are typically rarely arranged into a straight chain in a protein due to interaction between amino acid residues.

Figure 4:
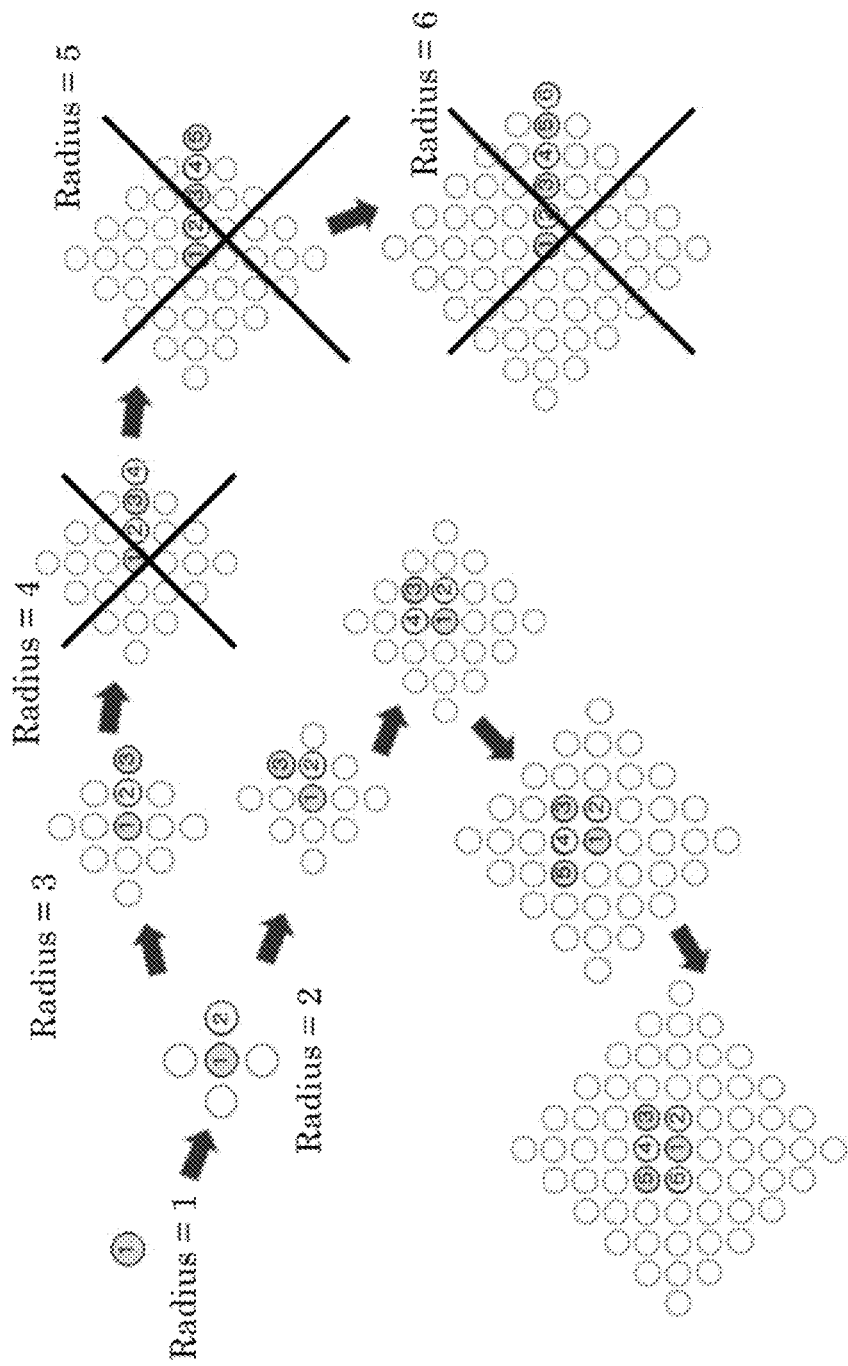
FIG. 4 is a conceptual view illustrating a state where a lattice space is limited according to the disclosed technology.

Therefore, a conformation of a protein can be determined without matching a radius r of a diamond lattice space with the number (n) of amino acid residues as illustrated in FIG. 4.

According to the disclosed technology, therefore, in the case where any of the compound groups is arranged in any of the lattices of the lattice space, followed by arranging a next compound group in the lattice space, a limited lattice space that is a space created by eliminating, from the lattice space, undesirable regions for the next compound group to be arranged, is generated, and a bit is assigned to each of lattice points, to which the compound groups can be arranged in the limited lattice space. As a result, the number of arithmetic bits or quantum bits used for a search of a predetermined compound is suppressed, and a compound having a large molecular weight can be searched.

For example, the compound groups are amino acid residues.

In the case where the compound groups are amino acid residues, examples of the compound include a protein.

Amino acid that is a base of an amino acid residue may be natural amino acid or synthetic amino acid. Examples of the natural amino acid include alanine, arginine, asparagine, aspartic acid, cysteine, glutamine, glutamic acid, glycine, histidine, isoleucine, leucine, lysine, methionine, phenyl alanine, proline, serine, threonine, tryptophan, tyrosine, valine, ß-alanine, and ß-phenylalanine. Examples of the synthetic amino acid include para-benzoylphenylalanine.

The number of amino acid residues in the protein is not particularly limited and may be appropriately selected depending on the intended purpose. For example, the number thereof may be from about 10 to about 30, or about several hundreds.

For example, the number thereof may be from about 10 to about 30 as long as the protein is a protein for middle molecule drug discovery.

One example of the disclosed technology will be described using examples of a device, flowcharts, etc., hereinafter.

Figure 5:
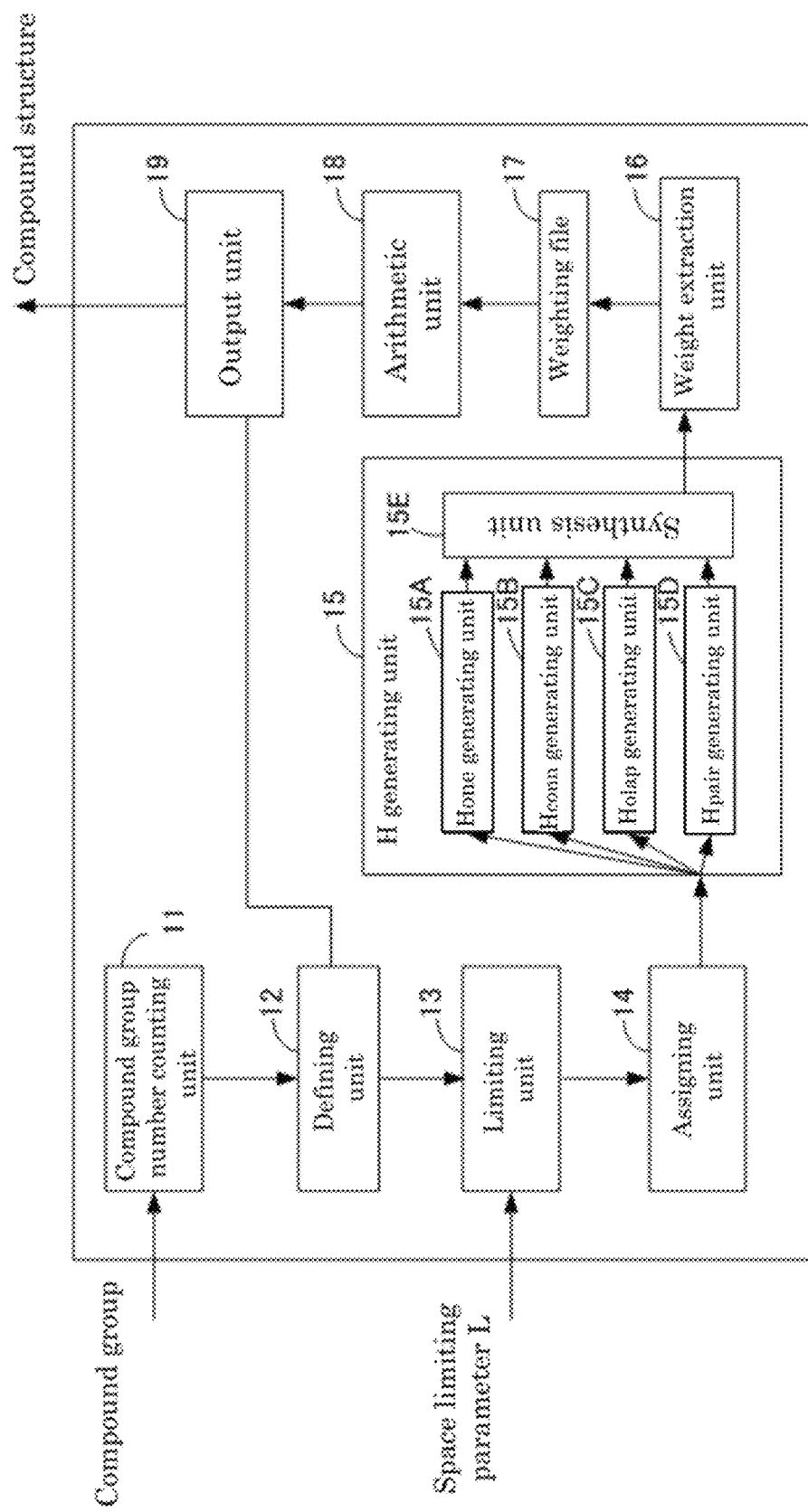
FIG. 5 is a view illustrating a structural example of the disclosed device for searching a compound.

A structural example of a device for searching a compound is illustrated in FIG. 5.

The device for searching a compound 10A illustrated in FIG. 5 includes a compound group number counting unit 11, a defining unit 12, a limiting unit 13, an assigning unit 14, a H generating unit 15, a weight extracting unit 16, a weight file creating unit 17, an arithmetic unit 18, and an outputting unit 19.

Figure 6:
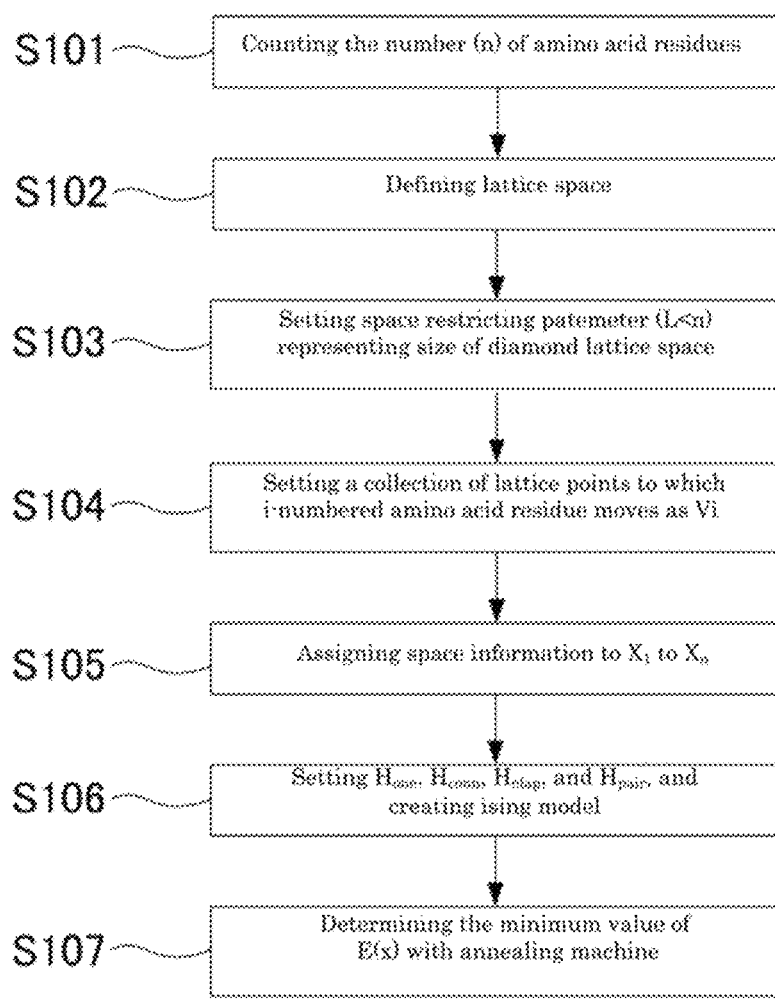
FIG. 6 is a flowchart for describing a method for searching a stable conformation of a protein using the device for searching a compound 10A of FIG. 5.

A flowchart for describing a method for searching a stable conformation of a protein using the device for searching a compound 10A of FIG. 5 is illustrated in FIG. 6.

First, the number (n) of amino acid residues (compound groups) constituting the input protein (an alignment of the amino acid residues) is counted by the compound group number counting unit 11 (S101).

Next, a lattice space that is a collection of lattices to which a plurality of the amino acid residues are sequentially arranged is defined by the defining unit 12 based on the number (n) of the amino acid residues (S102).

One example of the definition of the lattice space will be described. The lattice space is three dimensional, but a two dimensional lattice space is described as an example for simplicity.

Figure 7:
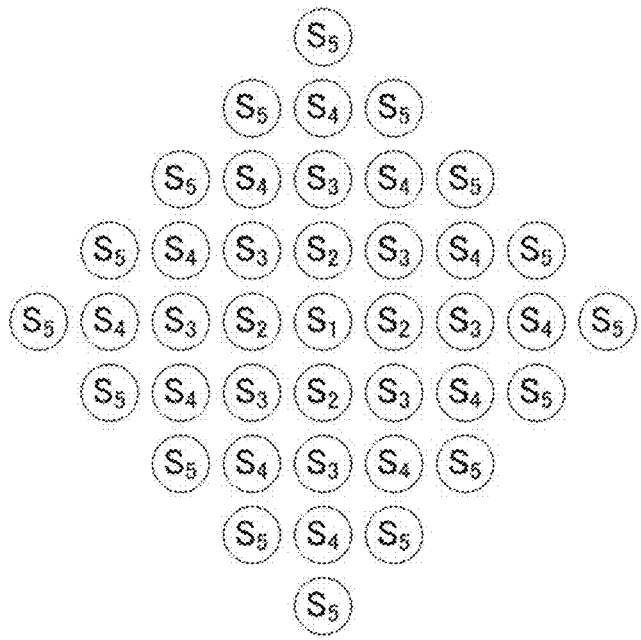
FIG. 7 is a view illustrating a case where each lattice within a radius r is $S_r$.

First, a collection of lattices within a radius r in a diamond lattice space is determined as a shell, and each lattice point is determined as $S_r$. Each lattice point $S_r$ is represented as in FIG. 7.

In the case where a limited lattice space is not generated unlike the disclosed technology, for example, collections $V_1$ to $V_5$ of lattice points to which amino acid residues of Nos. 1 to 5 are moved is represented as in FIGS. 8A to 8D.

Figure 8A:
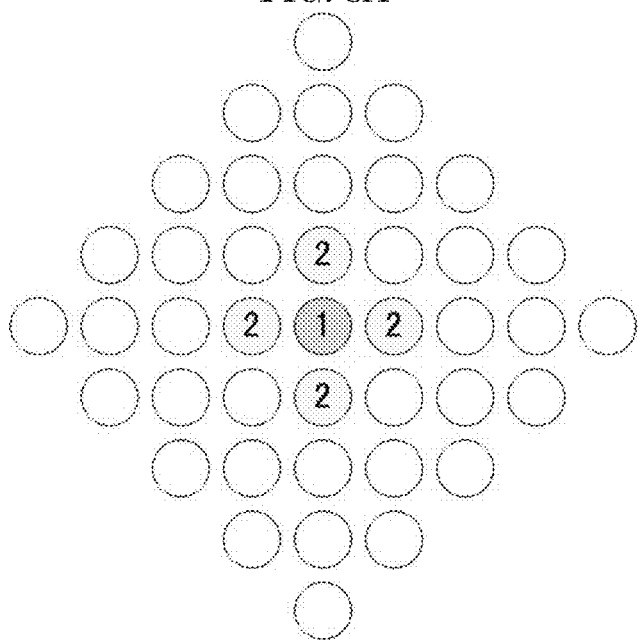
FIG. 8A is a view illustrating a collection of lattice points to which amino acid residues move in the case where a limited lattice space is not generated (part 1)
Figure 8B:
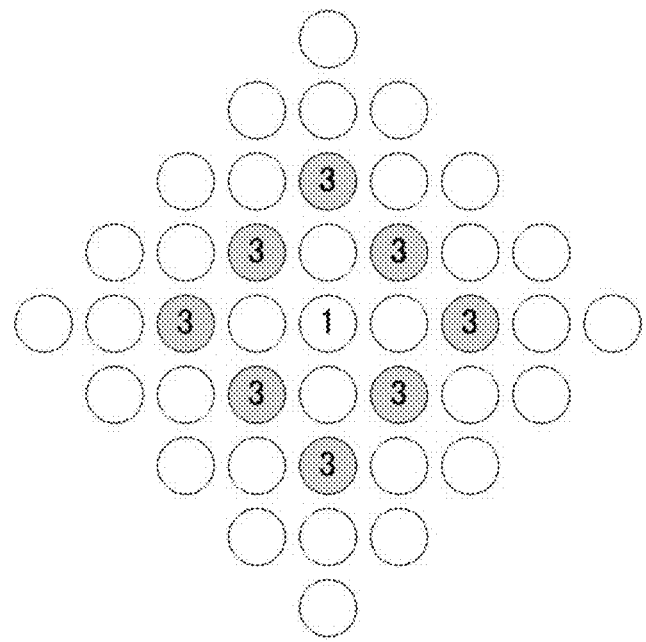
FIG. 8B is a view illustrating a collection of lattice points to which amino acid residues move in the case where a limited lattice space is not generated (part 2)
Figure 8C:
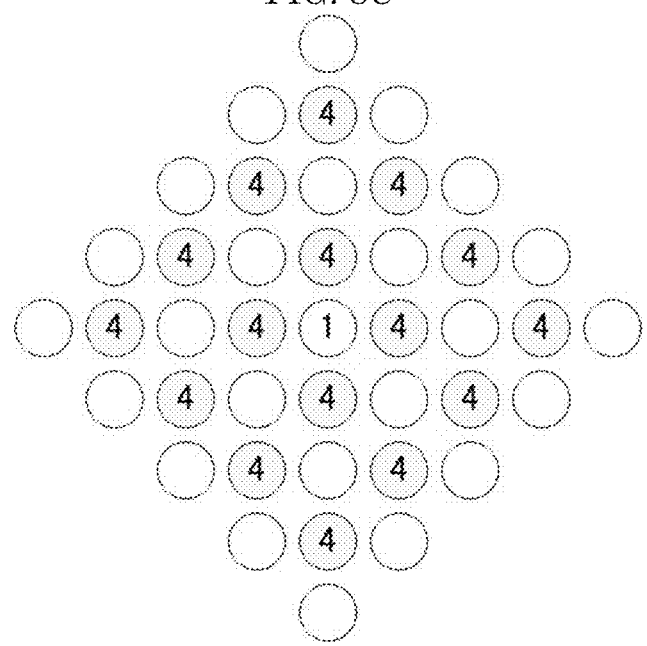
FIG. 8C is a view illustrating a collection of lattice points to which amino acid residues move in the case where a limited lattice space is not generated (part 3)
Figure 8D:
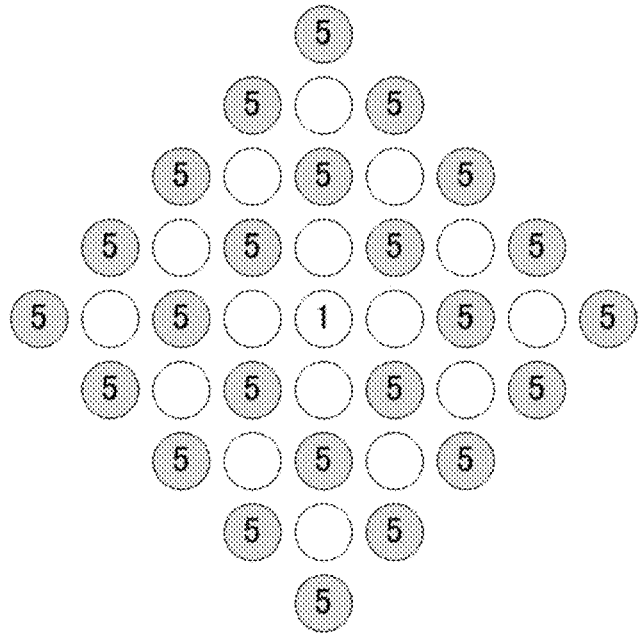
FIG. 8D is a view illustrating a collection of lattice points to which amino acid residues move in the case where a limited lattice space is not generated (part 4)

In FIG. 8A, $V_1=S_1$, and $V_2=S_2$.
In FIG. 8B, $V_3=S_3$.
In FIG. 8C, $V_4=S_2, S_4$.
In FIG. 8D, $V_5=S_3, S_5$.

Figure 9:
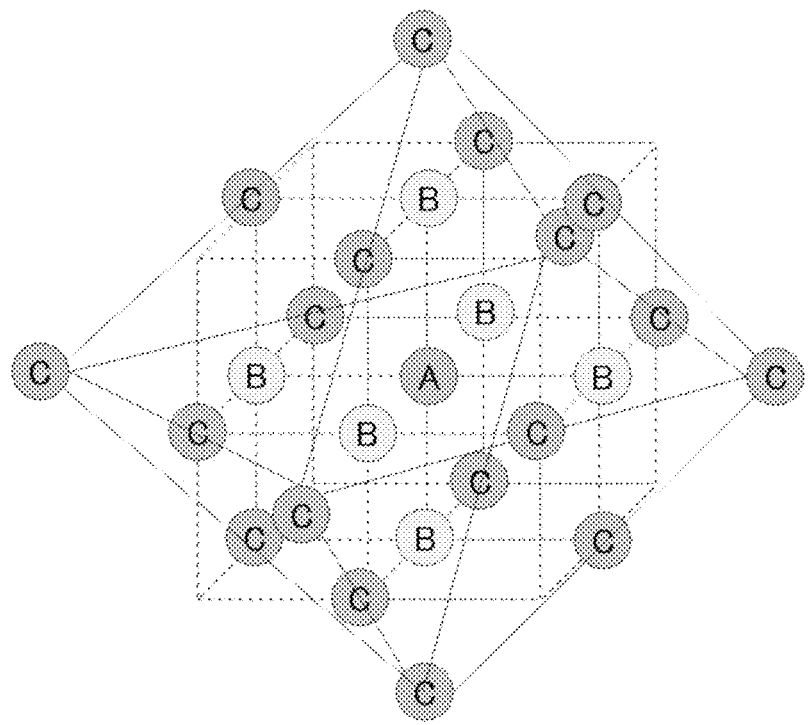
FIG. 9 is a view illustrating $S_1$, $S_2$, and $S_3$ three-dimensionally.
Figure 10A:
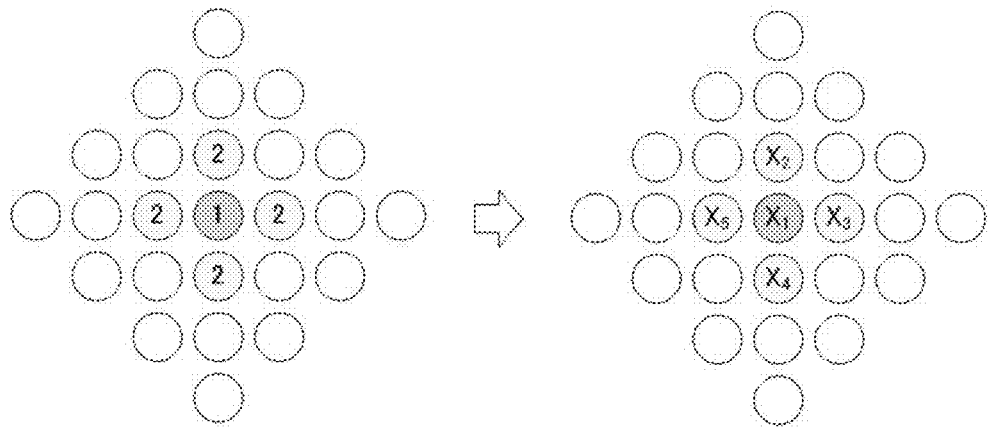
FIG. 10A is a view illustrating one example of a state where space information is assigned to each of bits $X_1$ to $X_n$ (part 1)
Figure 10B:
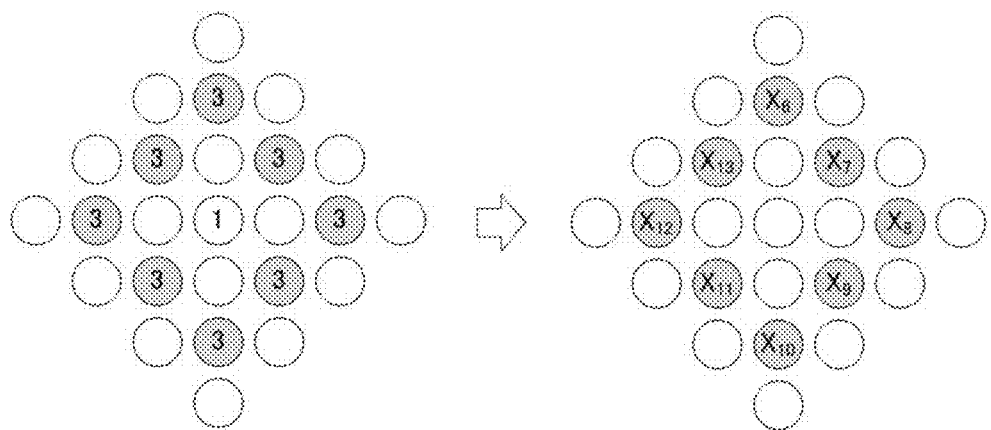
FIG. 10B is a view illustrating one example of the state where space information is assigned to each of bits $X_1$ to $X_n$ (part 2)
Figure 10C:
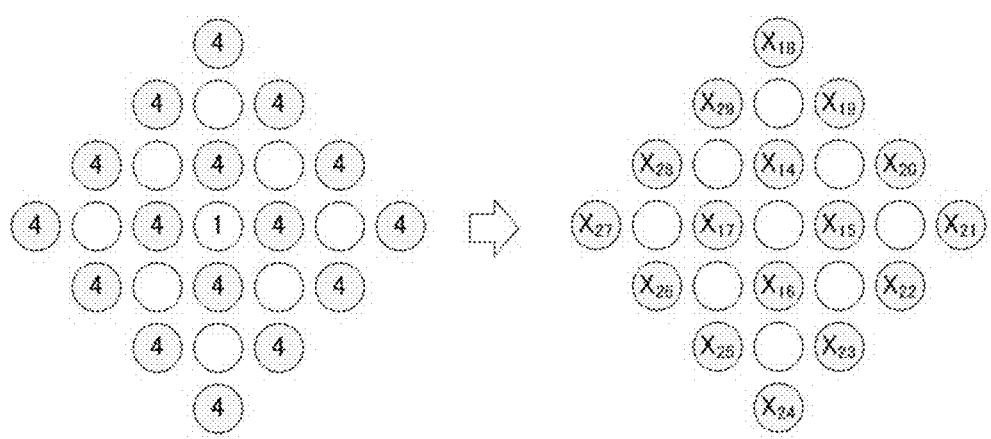
FIG. 10C is a view illustrating one example of the state where space information is assigned to each of bits $X_1$ to $X_n$ (part 3)
Figure 11:
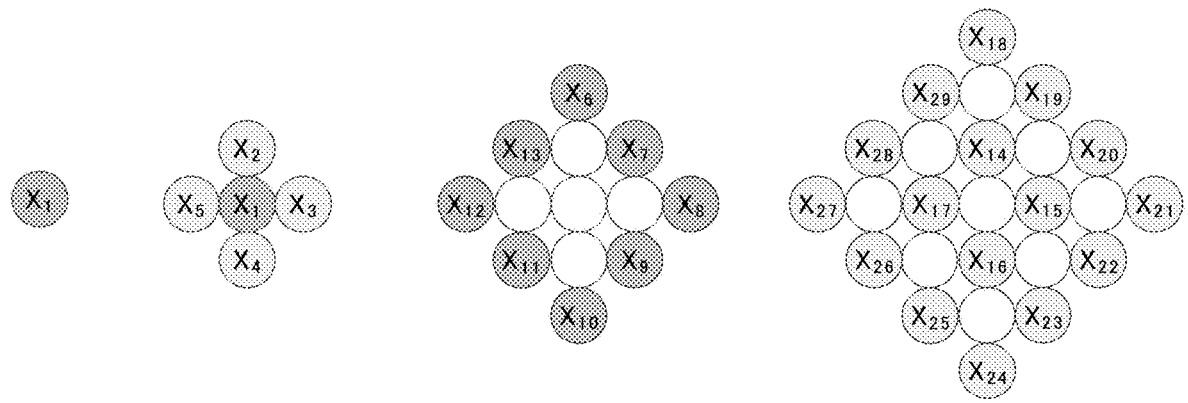
FIG. 11 is a view for describing $H_{one}$.
Figure 12:
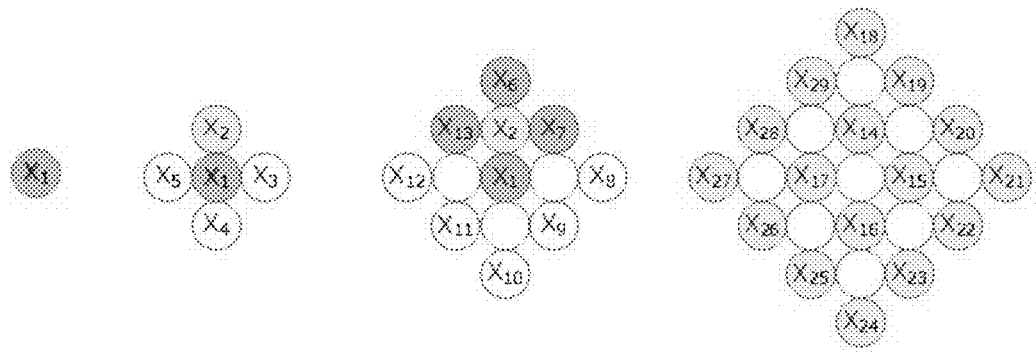
FIG. 12 is a view for describing $H_{conn}$.
Figure 13:
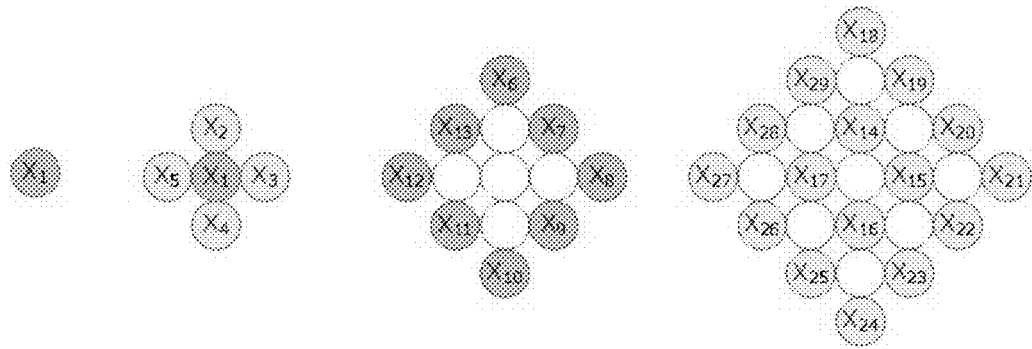
FIG. 13 is a view for describing $H_{olap}$.

Note that, when $S_1$, $S_2$, and $S_3$ are represented in three dimension, $S_1$, $S_2$, and $S_3$ represented as in FIG. 9. In FIG. 9, A=S1, B=$S_2$, and C=$S_3$.

In the case where a limited lattice space is not generated, a space $V_i$ used for i-numbered amino acid residues in a protein having amino acid residues in the number of n is represented by the following formula.

$$V_i = \bigcup_{r \in J} S_r$$

In the formula above, i={1, 2, 3, . . . n}.

In case of an odd numbered (i=odd number) amino acid residue, J={1, 3, . . . i}. In case of an even numbered (i=even number) amino acid residue, J={2, 4, . . . i}.

In the disclosed technology, meanwhile, in the case where any of the compound groups is arranged in any of the lattices of the lattice space, followed by arranging a next compound group in the lattice space, a limited lattice space that is a space created by eliminating, from the lattice space, undesirable regions for the next compound group to be arranged, is generated by the limiting unit 13. For example, a space limiting parameter L (L<n) representing a size of a diamond lattice space is set (S103), and a collection of lattice points to which i-numbered amino acid residue is move under the limit of the space limiting parameter L is determined as $V_i$ (S104).

$V_i$ that is the space for the i-numbered amino acid residue is represented by the following formula.

$$V_i = \bigcup_{r \in J} S_r$$

In the formula above, i={1, 2, 3, . . . n}.

When the space limiting parameter L is an even number, and i<L:
J={1, 3, . . . i} in case of an odd numbered (i=odd number) amino acid residue.
J={2, 4, . . . i} in case of an even numbered (i=even number) amino acid residue.

When the space limiting parameter L is an even number and i>L:
J={1, 3, . . . L-1} in case of an odd numbered (i=odd number) amino acid residue.
J={2, 4, . . . L} in case of an even numbered (i=even number) amino acid residue.

When the space limiting parameter L is an odd number and i<L:
J={1, 3, . . . i} in case of an odd numbered (i=odd number) amino acid residue.
J={2, 4, . . . i} in case of an even numbered (i=even number) amino acid residue.

When the space limiting parameter L is an odd number and i>L:
J={1, 3, . . . L} in case of an odd numbered (i=odd number) amino acid residue.
J={2, 4, . . . L-1} in case of an even numbered (i=even number) amino acid residue.

As described above, a space to which an amino acid residue is arranged is determined.

Next, the assigning unit 14 is configured to assign a bit to each of the lattice points to which a plurality of compound groups are arranged in the limited lattice space. Specifically, special information is assigned to each of bits $X_1$ to $X_n$ (S105). As illustrated in FIGS. 10B to 10E, specifically, a bit expressing presence of an amino acid residue in that position as 1 and absence of an amino acid residue as 0 is assigned with respect to a space to which each of amino acid residues is arranged. Note that, in FIGS. 10A to 10C, a plurality of $X_i$ are assigned to amino acid residues 2 to 4, but in reality one bit $X_i$ is assigned to one amino acid residue 1.

Next, $H_{one}$, $H_{conn}$, $H_{olap}$, and $H_{pair}$ are set and an Ising model obtained through conversion based on restriction conditions related to each lattice point is created (S106).

Setting of $H_{one}$, $H_{conn}$, $H_{olap}$, and $H_{pair}$ is performed in each of a $H_{one}$ generating unit 15A, a $H_{conn}$ generating unit 15B, a $H_{olap}$ generating unit 15C, and a $H_{pair}$ generating unit 15D of the H generating unit 15.

In the diamond encoding method, the entire energy can be expressed as follows.

$$E(x) = H = H_{one} + H_{conn} + H_{olap} + H_{pair}$$

In the formula above, $H_{one}$ is a restriction that there is only one from each of first to n-numbered amino acids.

$H_{conn}$ is a restriction that the first to n-numbered amino acids are all linked with one another.

$H_{olap}$ is a restriction that the first to n-numbered amino acids are not overlapped with one another.

$H_{pair}$ is a restriction representing an interaction between amino acids.

One example of each restriction is as follows.

Note that, in FIGS. 11 to 14 described below, $X_1$ is a position to which an amino acid residue of No. 1 can be arranged.

$X_2$ to $X_5$ are positions to which an amino acid residue of No. 2 can be arranged.

$X_6$ to $X_{13}$ are positions to which an amino acid residue of No. 3 can be arranged.

$X_{14}$ to $X_{29}$ are positions to which an amino acid residue of No. 4 can be arranged.

One example of $H_{one}$ is presented below.

$$H_{one} = \lambda_{one} \sum_{i=0}^{N-1} \sum_{x_a, x_b \in Q_i, a<b} x_a x_b$$

In the function above, $X_a$ and $X_b$ may be 1 or 0. Specifically, $H_{one}$ is a function that energy increases when any two of $X_2$, $X_3$, $X_4$, and $X_5$ are 1, because only one of $X_2$, $X_3$, $X_4$, and $X_5$ is 1 in FIG. 11, and is a term of penalty and becomes 0 when only one of $X_2$, $X_3$, $X_4$, and $X_5$ is 1.

Note that, in the function above, $\lambda_{one}$ is a weighting coefficient.

One example of $H_{conn}$ is presented below.

$$H_{conn} = \lambda_{conn}\left(N - 1 - \sum_{i=0}^{N-1} \sum_{x_d \in Q_i} \sum_{x_u \in \eta(x_d) \cap Q_{i+1}} x_d x_u\right)$$

In the function above, $X_d$ and $X_u$ may be 1 or 0. Specifically, $H_{conn}$ is a formula that energy decreases as long as any of $X_{13}$, $X_6$, or $X_7$ is 1 when $X_2$ is 1 in FIG. 12, and is a penalty term and becomes 0 when all of the amino acid residues are linked with one another.

Note that, in the function above, $\lambda_{conn}$ is a weighting coefficient. For example, the relationship of $\lambda_{one} > \lambda_{conn}$ is satisfied.

One example of $H_{olap}$ is presented below.

$$H_{olap} = \lambda_{olap} \sum_{v \in V} \sum_{x_a, x_b, \in \theta(v), a < b} x_a x_b$$

In the function above, $X_a$ and $X_b$ are 1 or 0. Specifically, $H_{olap}$ is a term generating a penalty when $X_{14}$ is 1 with $X_2$ being 1 in FIG. 13.

Note that, in the function above, $\lambda_{olap}$ is a weighting coefficient.

One example of $H_{pair}$ is presented below.

$$H_{pair} = \frac{1}{2} \sum_{i=0}^{N-1} \sum_{x_a \in Q_i} \sum_{x_b \in \eta(x_a)} P_{\omega(x_a)\omega(x_b)} x_a x_b$$

In the function above, $X_a$ and $X_b$ may be 1 or 0. Specifically, $H_{pair}$ is a function that energy decreases due to interaction $P_{\omega(x1)\omega(x15)}$ between the amino acid residue of $X_1$ and the amino acid residue of $X_{15}$ when $X_{15}$ is 1 with $X_1$ being 1 in FIGS. 14A and 14B. The interaction $P_{\omega(x1)\omega(x15)}$ is determined by a combination of two amino acid residues. For example, the interaction $P_{\omega(x1)\omega(x15)}$ is determined with reference to Miyazawa-Jernigan (MJ) matrix.

Next, H is calculated by synthesizing $H_{one}$, $H_{conn}$, $H_{olap}$, and $H_{pair}$ by the synthesizing unit 15E.

Next, a weighting coefficient ($\lambda_{one}$, $\lambda_{conn}$, and $\lambda_{olap}$) of each functions above is extracted by the weight extracting unit 16.

Next, a weight file corresponding to the extracted weight coefficient is created by the weight file creating unit 17. For example, the weight file is a matrix. In case of $2X_1X_2 + 4X_2X_3$, for example, the weight file is a matrix file as illustrated in FIG. 15.

The following energy formula of the Ising model can be expressed by using the created weight file.

$$E(x) = -\sum_{\langle i,j \rangle} W_{ij} x_i x_j - \sum_i b_i x_i$$

In the function above, the states $X_i$ and $X_j$ may be 0 or 1, where 0 means absence and 1 means presence. $W_{ij}$ that is a first term of the right side is a weighting coefficient.

The first term of the right side is the integration of the product of the state of two neuron circuits and the weighting value for all selectable combinations of two neuron circuits from the whole neuron circuits without any omission or overlap.

Moreover, the second term of the right side is the integration of the product of the bias value and state of each of the whole neuron circuits. $b_i$ is a bias value of the i-numbered neuron circuit.

Next, the arithmetic unit 18 (annealing machine) executes a ground state search of the Ising model converted based on the restriction conditions related to each of the lattice points according to simulated annealing to thereby calculate the minimum energy of the Ising model (S107).

The arithmetic unit 18 (annealing machine) may be any of a quantum annealing machine, a semiconductor annealing machine using a semiconductor technology, or simulated annealing executed by software using a central processing unit (CPU) or a graphics processing unit, if the computer for use is a computer employing an annealing system for performing a ground state search of an energy function represented by the Ising model.

The calculated result is output from the outputting unit 19. The result may be output as a conformation view of a protein, or is output as coordinate information of each amino acid residues constituting a protein.

One example of simulated annealing and the arithmetic unit 18 (annealing machine) will be described below.

Simulated annealing (SA) is a kind of Monte Carlo methods, and a method for stochastically determining using a random numerical value. In the description below, a problem for minimizing a value of an evaluation function to be optimized is taken as an example, and the value of the evaluation function is called energy. In case of maximization, a plus or minus sign of the evaluation function may be changed.

Starting with an initial state where one discrete value is assigned to each variable, a state that is close to the initial state (e.g., a state where only one variable is changed) is selected from the current state (combinations of values of the variables), and then state transition thereof is studied. An energy change for the state transition is calculated, and whether the state transition is adapted to change the state or the original state is retained without adapting the state transition is determined stochastically depending on the calculated value. When the adaption probability of a case where energy reduces is selected to be larger than the adaption probability of a case where energy increases, the state change occurs in the tendency that the energy reduces on average, and it is expected that the state transits to an appropriate state over time. Then, ultimately, it is possible to obtain an approximation solution that gives energy close to an optimum solution or an optimum value. If the case where energy reduces is adopted deterministically and the case where energy increases is not adapted, the energy change is in the state of weakly decreasing with respect to time, but the change will stop once the local solution is reached. Since there are a large number of local solutions in the discrete optimization problem as described above, it is most likely that the state is trapped by a local solution that is not very close to an optimum value. Accordingly, it is important to stochastically determine whether to adapt.

It is proved in the simulated annealing that the state reaches the optimum solution with the limit of infinite time (the number of iteration) when the adaptation (tolerance) probability of the state transition is determined as follows.

(1) With respect to an energy change (energy decrease) value (−ΔE) along with the state transition, acceptance probability p of the state transition is determined by any of the following functions f ( ).

$$p(\Delta E, T) = f(-\Delta E/t) \quad \text{(Formula 1-1)}$$

$$f_{metro}(x) = \min(1, e^x)(\text{Metropolis method}) \quad \text{(Formula 1-2)}$$

$$f_{Gibbs}(x) = \frac{1}{1+e^{-x}}(\text{Gibbs method}) \quad \text{(Formula 1-3)}$$

In the formula above, T is a parameter called a temperature value, which is changed as follows.
(2) The temperature value T is logarithmically decreased relative to the number of iteration t as represented by the following formula.

$$T = \frac{T_0 \log(c)}{\log(t+c)} \quad \text{(Formula 2)}$$

In the formula above, $T_0$ is an initial temperature value, and is desired to be sufficiently large depending on a problem.

In the case where acceptance probability represented by the formula of (1) is used, once the state reaches a steady state after sufficient iterations, occupancy probability of each state follows the Boltzmann distribution for a thermal equilibrium state in thermodynamics.

As the temperature is gradually lowered from a high temperature, occupancy probability of a low energy state increases. Therefore, a low energy state is supposed to be obtained when the temperature is sufficiently reduced. The state as described above is very similar to a state change occurred when a material is developed. Therefore, the method described above is called simulated annealing. The stochastic occurrence of the state transition of energy increase is equivalent to thermal excitation in physics.

Figure 16:
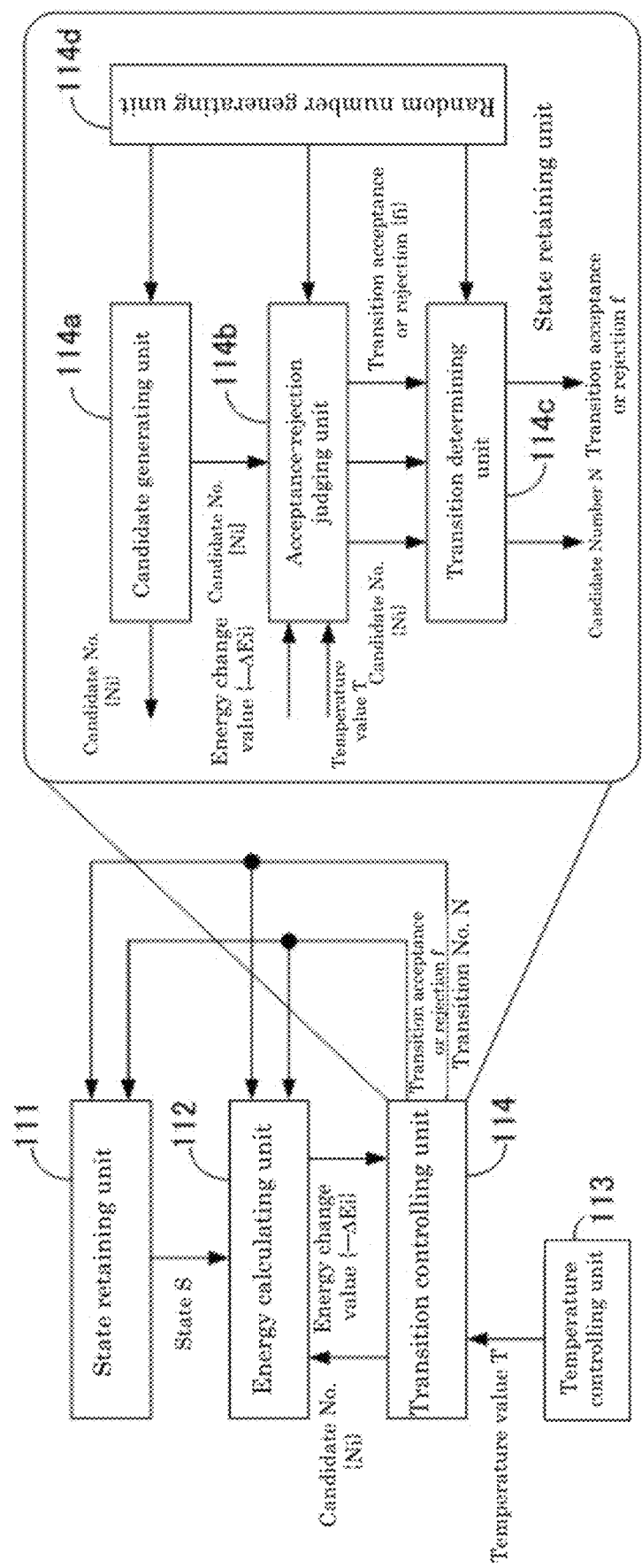
FIG. 16 is a view illustrating a conceptual structure of an optimizing device (arithmetic unit) used for simulated annealing.

An optimizing device (arithmetic unit 18) for performing simulated annealing is illustrated in FIG. 16. The descriptions below include a case where a plurality of candidates of state transitions are generated, but a transition candidate is generated one by one in the original basic simulated annealing.

An optimizing device 100 includes a state retaining unit 111 configured to retain a current state S (a plurality of state variable values). Moreover, the optimizing device 100 includes an energy calculating unit 112 configured to calculate an energy change value {−ΔEi} of each state transition when a state transition occurs from the current state S due to a change of any of the state variable values. Moreover, the optimizing device 100 includes a temperature controlling unit 113 configured to control a temperature value T and a transition controlling unit 114 configured to control a state transition.

The transition controlling unit 114 is configured to stochastically determine whether any of the state transitions is adapted or not according to the correlation between the energy change value {−ΔEi} and the thermal excitation energy based on the temperature value T, the energy change value {−ΔEi}, and the random numerical value.

The transition controlling unit 114 is further subdivided. The transition controlling unit 114 includes a candidate generating unit 114a configured to generate candidates of state transition, and a judging unit 114b configured to stochastically judge on each candidate whether the state transition is allowed or not based on the energy change value {−ΔEi} and temperature value T thereof. The transition controlling unit 114 further includes a transition determining unit 114c configured to determine the candidate to be adapted among the allowed candidates, and a random number generating unit 114d configured to generate probability variables.

An operation of one iteration is as follows. First, the candidate generating unit 114a generates one or more candidates (candidate number {Ni}) of state transition from the current state S retained in the state retaining unit 111 to the next state. The energy calculating unit 112 calculates an energy change value {−ΔEi} for each of state transitions listed as candidates using the current state S and the candidates of state transition. The judging unit 114b accepts the state transition with the acceptance probability of the formula of (1) above according to the energy change value {−ΔEi} of each state transition using the temperature value T generated by the temperature controlling unit 113 and the probability variable (random numerical value) generated by the random number generating unit 114d. Then, the judging unit 114b outputs acceptance or rejection {fi} of each state transition. In the case where there are a plurality of the accepted state transitions, the transition determining unit 114c randomly selects one of the accepted state transitions using the random numerical value. The transition determining unit 114c outputs the transition number N of the selected state transition and acceptance or rejection of the transition f. In the case where there is the accepted state transition, the value of the state variable stored in the state retaining unit 111 is updated according to the adapted state transition.

The iteration described above is started from an initial state and repeated with decreasing the temperature value by the temperature controlling unit 113. When the finishing judgement conditions, such as reaching the certain number of iterations, or the energy being dropped below a certain value, are satisfied, the operation is completed. The answer output by the optimizing device 110 is the state at the time of the finish.

Figure 17:
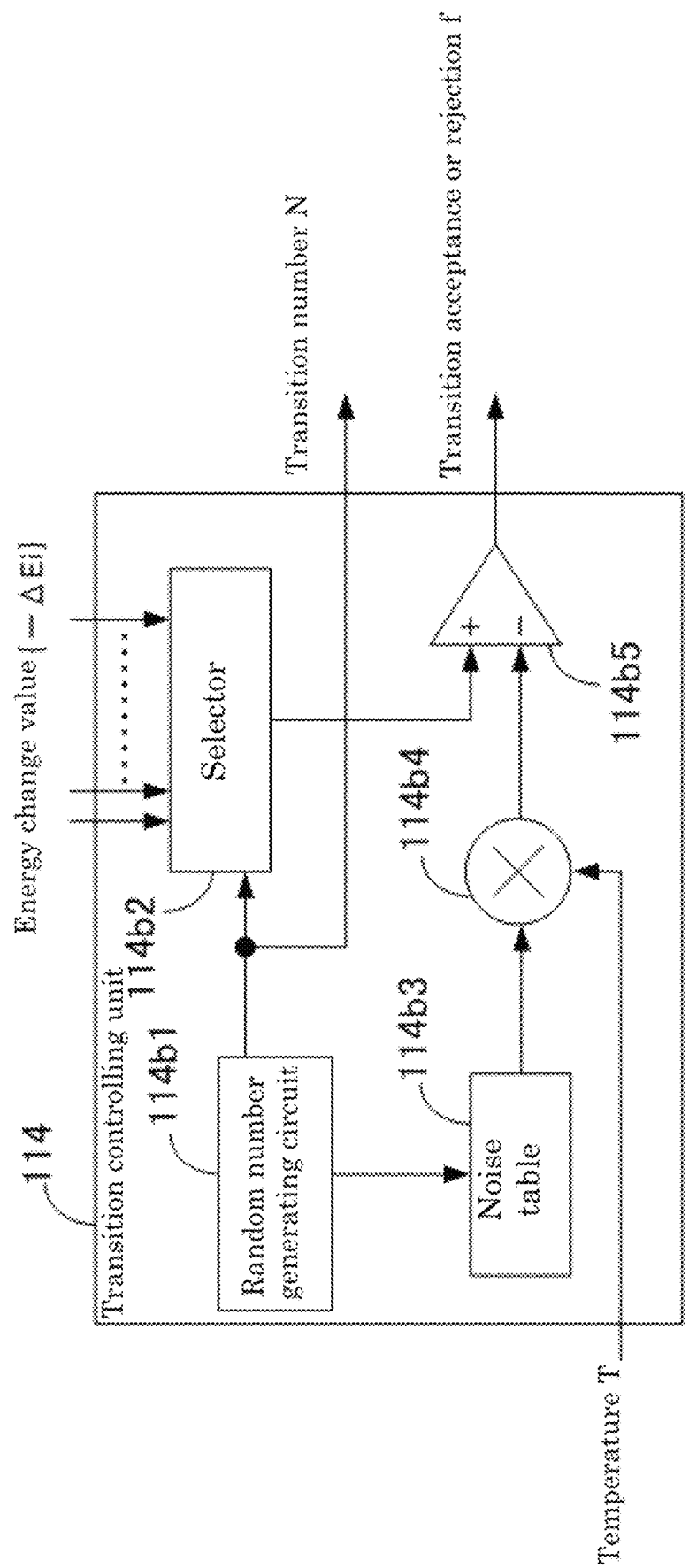
FIG. 17 is a block diagram of a circuit level of a transition controlling unit.

FIG. 17 is a block diagram of a circuit level of a structural example of arithmetic part used for a transition controlling unit, particularly a judging unit, in typical simulated annealing where a candidate is generated one by one.

A transition controlling unit 114 includes a random number generator 114b1, a selector 114b2, a noise table 114b3, a multiplier 114b4, and a comparator 114b5.

The selector 114b2 is configured to select the value corresponding to the transition number N that is a random numerical value generated by the random number generator 114b1 among the energy change values {−ΔEi} calculated for candidates of each state transition, and then output the value.

Functions of the noise table 114b3 will be described later. As the noise table 114b3, for example, a memory, such as a random access memory (RAM), and a flash memory, can be used.

The multiplier 114b4 outputs a product (corresponding to the above-described thermal excitation energy) obtained by multiplying the value output by the noise table 114b3 with the temperature value T.

The comparator 114b5 outputs, as transition acceptance or rejection f, a comparison result obtained by comparing the product result output by the multiplier 114b4 and the energy change value −ΔE selected by the selector 114b2.

The transition controlling unit 114 illustrated in FIG. 17 basically has the above-mentioned functions as they are, but a mechanism for accepting state transition with the acceptance probability represented by the formula (1) has not yet been described. Therefore, the mechanism will be supplementary described.

The circuit that outputs 1 with the acceptance probability p and 0 with (1−p) has two inputs A and B, can be realized by inputting the acceptance probability p to the input A of the comparator and a uniform random number having the value in the interval [0, 1] to the input B of the comparator where the comparator outputs 1 when A>B and outputs 0 when A<B. Accordingly, the above-described function can be realized by inputting the value of the acceptance probability p calculated from the energy change value and the temperature value T using the formula of (1) to the input A of the comparator.

Specifically, the above-described function can be realized with the circuit that outputs 1 when f(ΔE/T) is larger than u, where f is the function represented by the formula of (1) and u is a uniform random number having the value of the interval [0, 1].

The circuit may be as it is, but the same function can be also realized by performing the following deformation. The magnitude relationship of two numbers does not change when the same monotone increasing function is given the two numbers. Therefore, output does not change even when the same monotone increasing function is gives two inputs of the comparator. It can be understood that a circuit outputting 1 when −ΔE/T is larger than $f^{-1}(u)$ is acceptable when an inverse function $f^{-1}$ off is used as the monotone increasing function. Since the temperature value T is a positive value, moreover, a circuit outputting 1 when −ΔE is larger than $Tf^{-1}(u)$ is acceptable. The noise table 114b3 in FIG. 17 is a conversion table for realizing the inverse function $f^{-1}(u)$, and a table for outputting a value of the following function with respect to an input of discretized interval [0, 1].

$$f_{metro}^{-1}(u) = \log(u) \qquad \text{(Formula 3-1)}$$

$$f_{Gibbs}^{-1}(u) = \log\left(\frac{u}{1-u}\right) \qquad \text{(Formula 3-2)}$$

The transition controlling unit 114 also includes a latch configured to retain judgement results etc., a state machine configured to generate timing thereof, etc., but the above-mentioned units are omitted in FIG. 17 in order to simplify the illustration.

Figure 18:
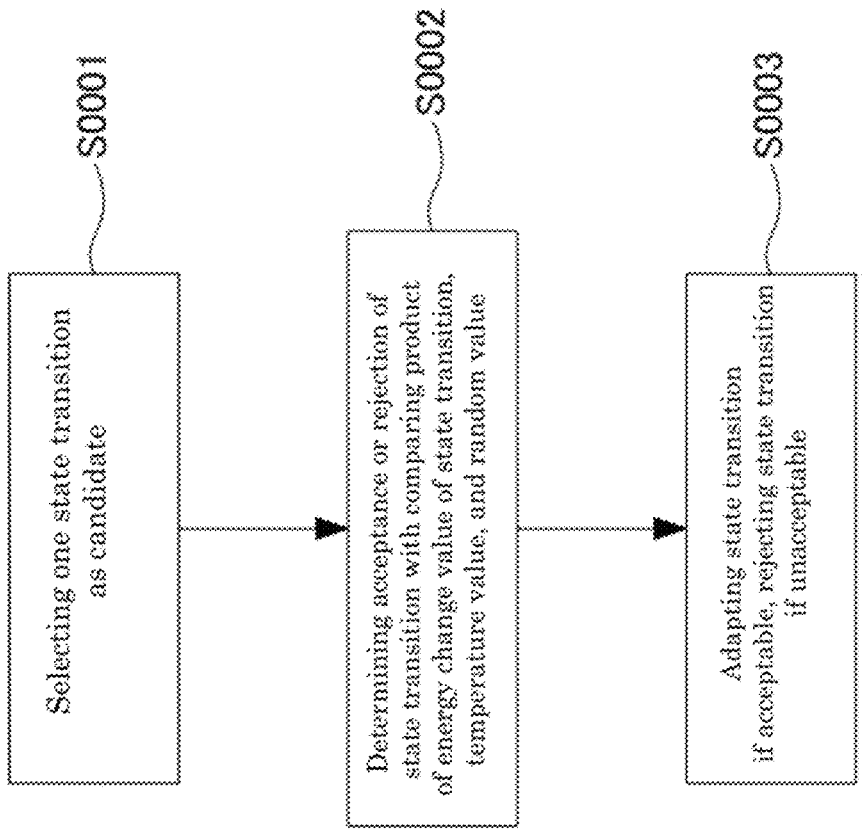
FIG. 18 is a diagram illustrating an operation flow of a transition controlling unit.

FIG. 18 illustrates an operation flow of the transition controlling unit 114. The operation flow includes a step for selecting one state transition as a candidate (S0001), a step for determining acceptance or rejection of the state transition with comparing a product of the energy change value of the state transition, temperature value, and random numerical value (S0002), and a step for adapting the state transition if the state transition is acceptable and rejecting if the state transition is not acceptable (S0003).

Figure 19:
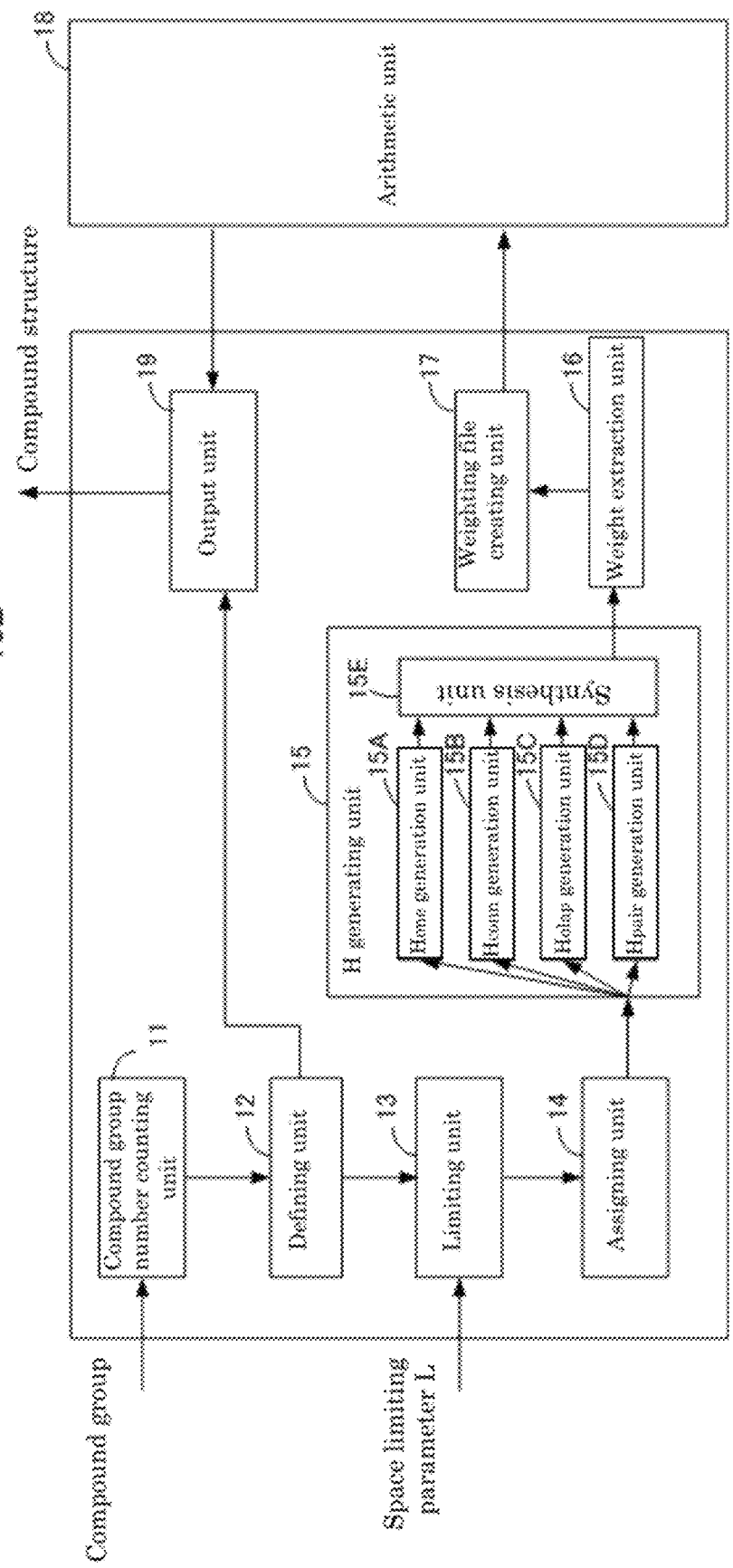
FIG. 19 is a view illustrating another structural example of the disclosed device for searching a compound.

Note that, the device for searching a compound 10A illustrated in FIG. 5 is an example where the arithmetic unit 18 is disposed in the same space with limiting unit 13 etc., but the disclosed device for searching a compound may include the arithmetic unit 18 that is spatially away from the limiting unit 13 etc. like the device for searching a compound 10B illustrated in FIG. 19.

Next, another example of the disclosed technology will be described using another device example, a flowchart, etc.

Figure 20:
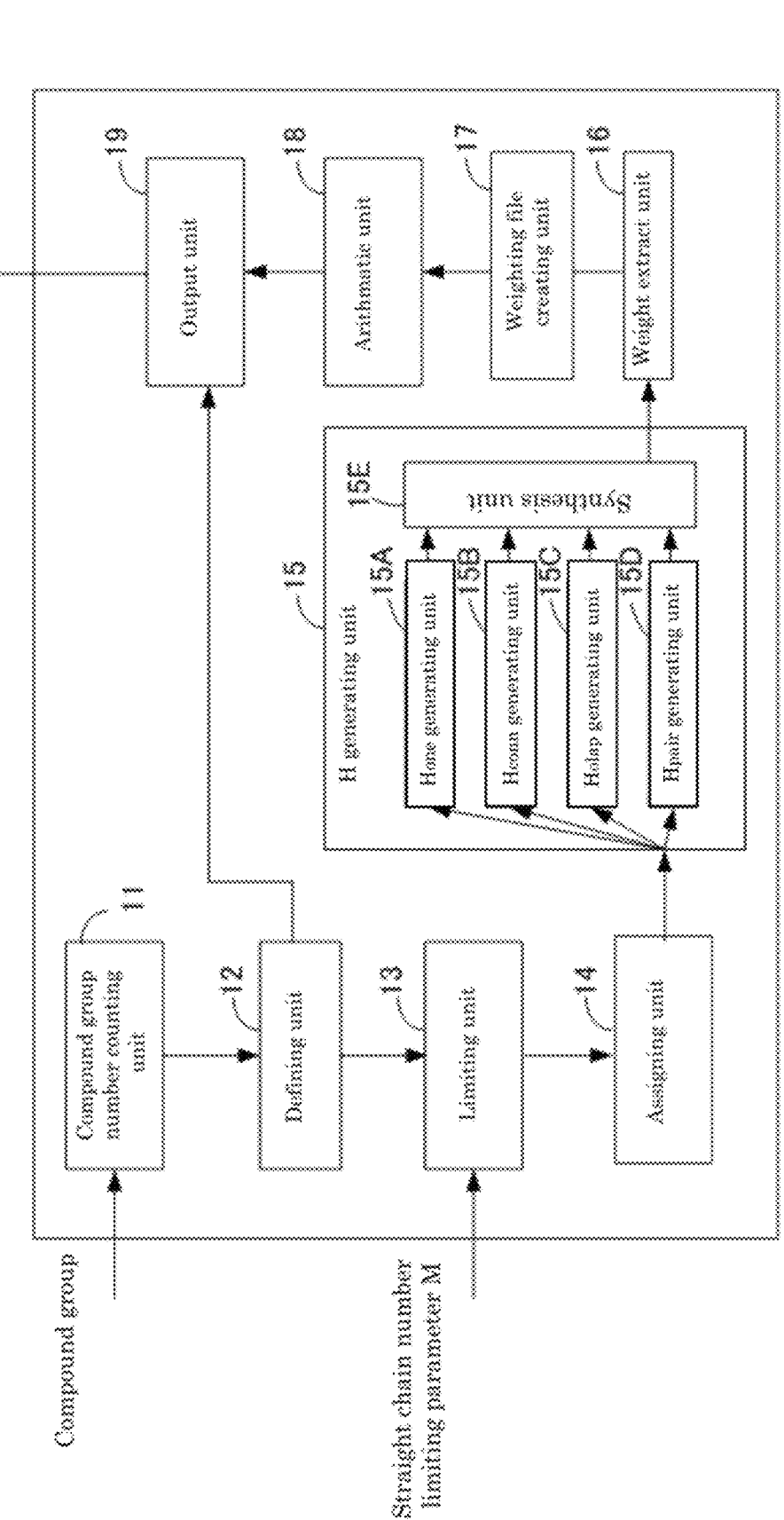
FIG. 20 is a view illustrating another structural example of the disclosed device for searching a compound.

A structural example of the device for searching a compound is illustrated in FIG. 20.

A device for searching a compound 10C illustrated in FIG. 20 includes a compound group number counting unit 11, a defining unit 12, a limiting unit 13, an assigning unit 14, a H generating unit 15, a weight extracting unit 16, a weight file creating unit 17, an arithmetic unit 18, and an outputting unit 19.

Figure 21:
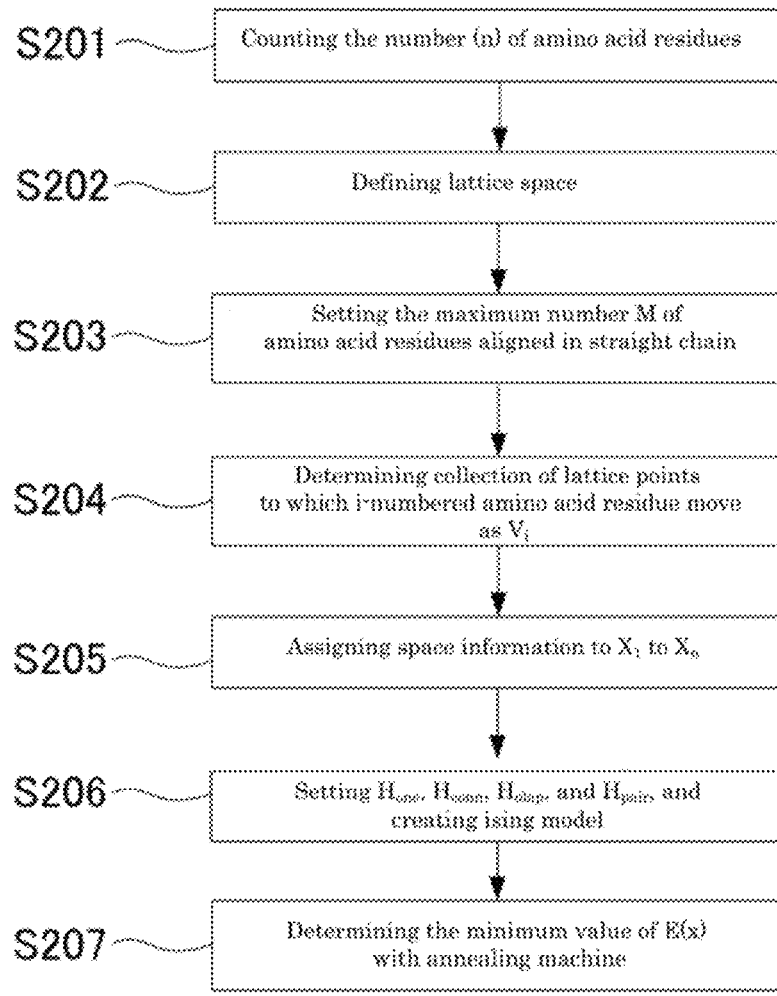
FIG. 21 is a flowchart illustrating a method for searching a stable conformation of a protein using the device for searching compound 10C of FIG. 20.

A flowchart illustrating a method for searching a stable conformation of a protein using the device for searching a compound 10C of FIG. 20 is illustrated in FIG. 21.

Each unit of the device for searching a compound 10C illustrated in FIG. 20 is identical to each unit of the device for searching a compound 10A illustrated in FIG. 5 except the limiting unit 13.

In the flowchart of FIG. 21, the step S201 corresponds to the step S101 of the flowchart of FIG. 6, the step S202 corresponds to the step S102, the step S204 corresponds to the step S104, the step S205 corresponds to the step S105, the step S206 corresponds to the step S106, and the step S207 corresponds to the step S107.

Therefore, the descriptions are given with focusing on the limiting unit 13 and the step S203.

By setting the maximum number M (straight chain number limiting parameter M) of amino acid residues aligned in a straight chain (S203), the limiting unit 13 generates a limited lattice space obtained by removing, from the lattice space, undesirable regions for the next compound group to be arranged, in the case where any of a plurality of compound groups is arranged in any lattice of the lattice space, followed by arranging the next compound group in the lattice space.

As described earlier, amino acid residues are typically rarely aligned in a straight chain due to interaction between the amino acid residues.

Therefore, the number of arithmetic bits or quantum bits can be suppressed by setting the maximum number M (straight chain number limiting parameter M) of amino acid residues aligned in a straight chain, and eliminating regions where the amino acid residues are not be disposed under the restrictions above to thereby generate a limited lattice space. Naturally, M is smaller than the number (n) of amino acid residues (M<n).

Figure 22:
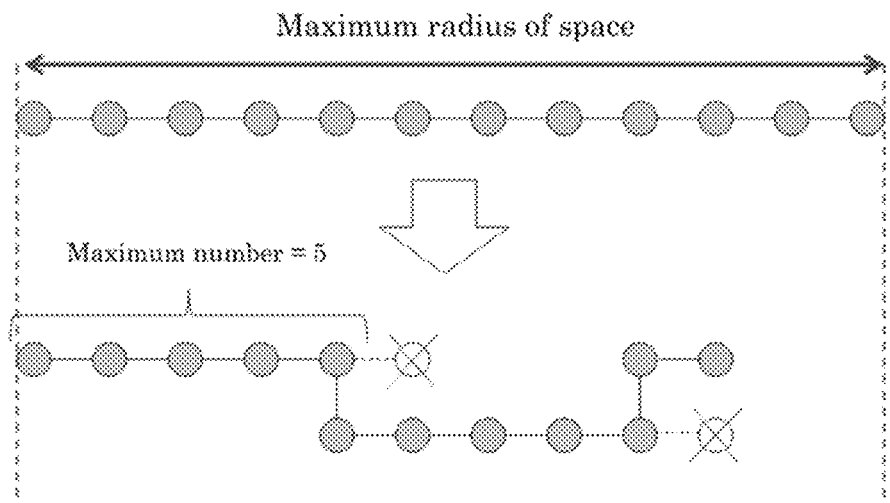
FIG. 22 is a view for describing the limit in an alignment of amino acid residues when a straight chain number limiting parameter M (part 1) is set.

For example, when the straight chain number limiting parameter M is set to 5, as illustrated in FIG. 22, the number of amino acid residues aligned in a straight chain is 5 as the maximum number.

Figure 23:
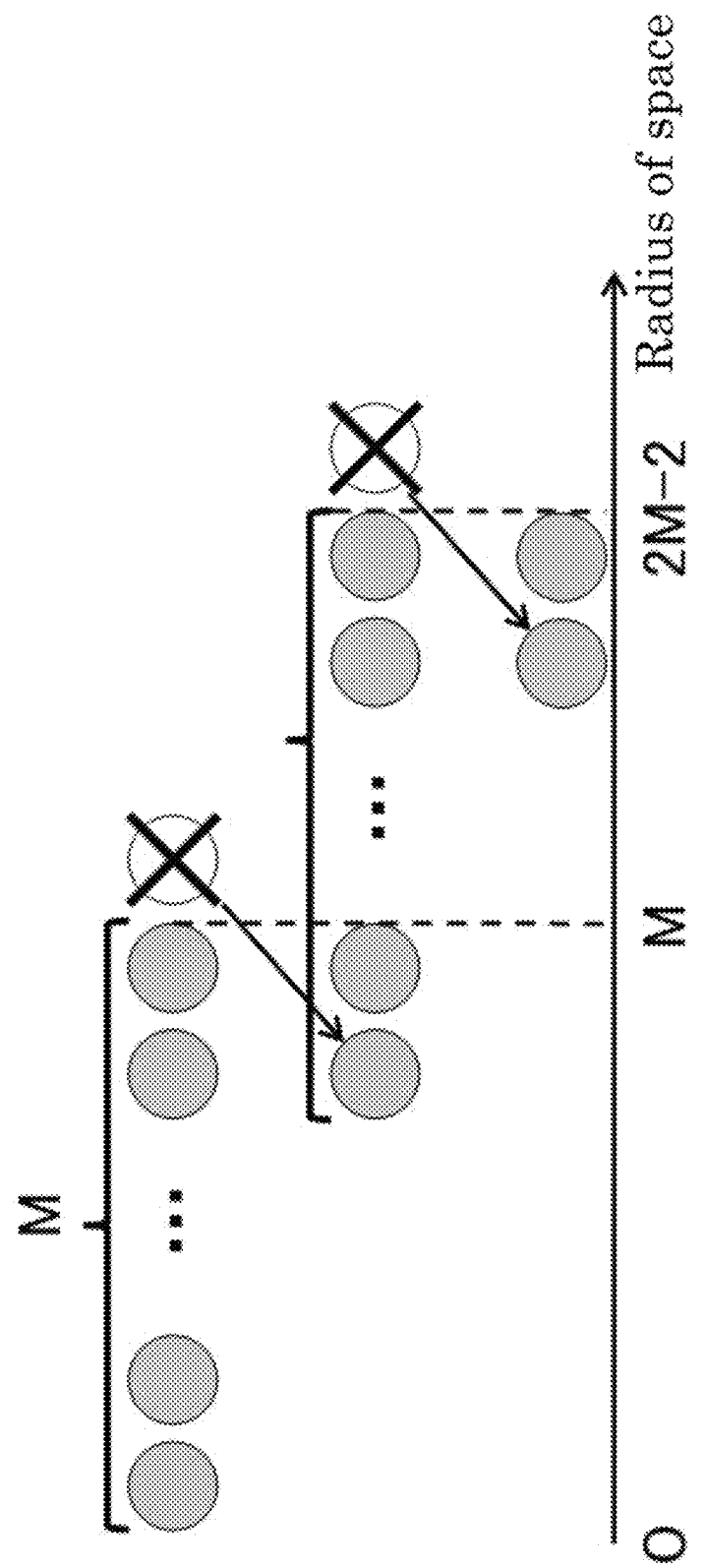
FIG. 23 is a view for describing the limit in an alignment of amino acid residues when a straight chain number limiting parameter M (part 2) is set.

When the straight chain number limiting parameter M is set, the limited lattice space increases as the number of the amino acid residues increases as illustrated in FIG. 23. Specifically, the maximum lattice space K is determined by the following formula when the straight chain limiting parameter M is used for the amino acid residues in the number of n.

$$K = \left\lfloor \frac{n-M}{M} \right\rfloor \times (M-2) + \text{MAX}(n \bmod [M] - 2, 0) + M$$

A space limiting parameter L (L<n) may be used in combination for generation of a limited lattice space. In this case, it is preferable that L≤K be satisfied.

Next, another example of the disclosed technology will be described using another device example, a flowchart, etc.

Figure 24:
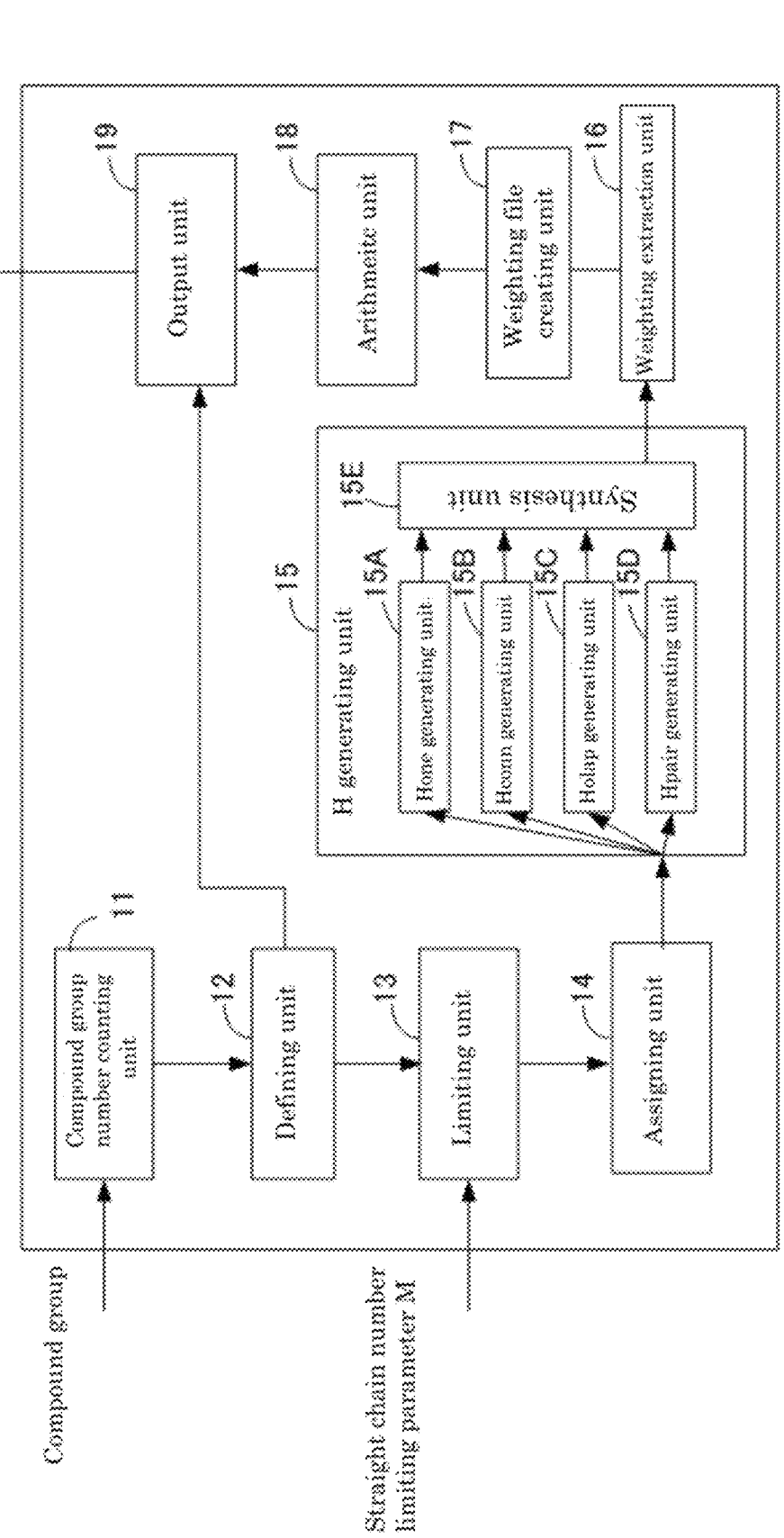
FIG. 24 is a view illustrating another structural example of the disclosed device for searching a compound.

A structural example of the device for searching a compound is illustrated in FIG. 24.

The device for searching a compound 10D illustrated in FIG. 24 includes a compound group number counting unit 11, a defining unit 12, a limiting unit 13, an assigning unit 14, a H generating unit 15, a weight extracting unit 16, a weight file creating unit 17, an arithmetic unit 18, and an outputting unit 19.

Figure 25:
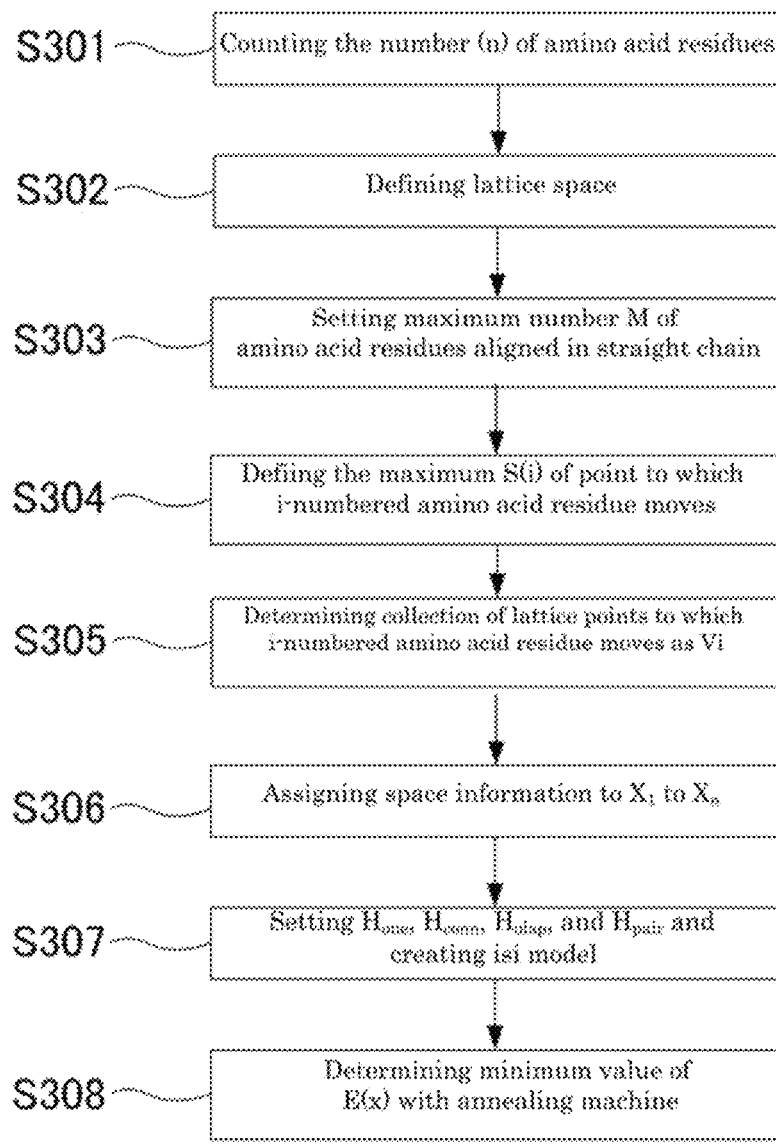
FIG. 25 is a flowchart illustrating a method for searching a stable conformation of a protein using the device for searching a compound 10D of FIG. 24.

A flowchart for searching a stable conformation of a protein using the device for searching a compound 10D of FIG. 24 is illustrated in FIG. 25.

Each unit of the device for searching compound 10D illustrated in FIG. 24 is identical to each unit of the device for searching a compound 10C illustrated in FIG. 20, except the limiting unit 13.

In the flowchart of FIG. 25, the step S301 corresponds to the step S201 of the flowchart of FIG. 21, the step S302 corresponds to the step S202, the step S303 corresponds to the step S203, the step S305 corresponds to the step S204, the step S306 corresponds to the step S205, the step S307 corresponds to the step S206, and the step S308 corresponds to the step S207.

Therefore, descriptions are given with focusing on the limiting unit 13 and the step S304.

In the case where any of a plurality of compound groups is arranged in any lattice of a lattice space followed by arranging a next compound group in the lattice space, the limiting unit 13 creates a limited lattice space, which is obtained by eliminating undesirable regions for the next compound group to be arranged from the lattice space, by setting the maximum number M (straight chain limiting parameter M) of amino acid residues aligned in a straight chain (S303), and moreover defining the maximum S(i) of the site to which i-numbered amino acid residue is moved (S304).

When the straight chain number limiting parameter M is used, a space radius r of each amino acid residue is for example as presented in Table 1 with M=5 (K=8), n=11, and L=K.

TABLE 1

| Amino acid residue | 1 | 2 | 3 | 4 | 5 | 6 | 7 | 8 | 9 | 10 | 11 |
|---|---|---|---|---|---|---|---|---|---|---|---|
| R Radius r' | 1 | 2 | 3 | 4 | 5 | 6 | 7 | 8 | 8 | 8 | 8 |
| actually estimated | 1 | 2 | 3 | 4 | 5 | 4 | 5 | 6 | 7 | 8 | 7 |

Figure 26:
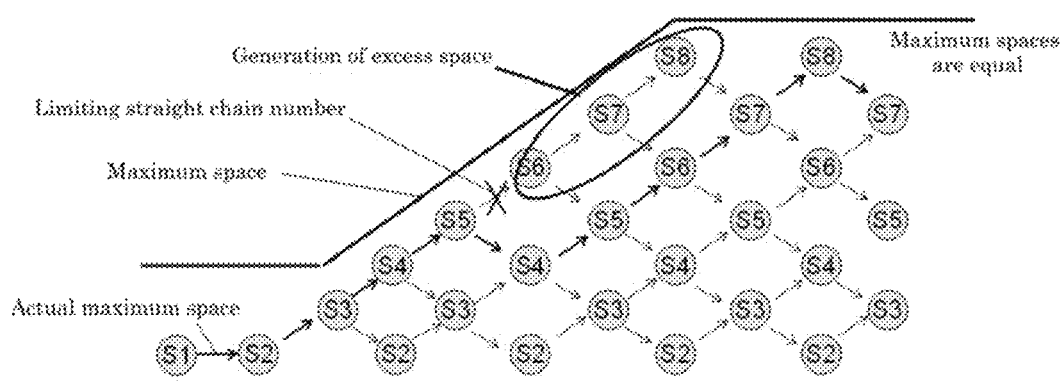
FIG. 26 is a view for describing the maximum space when a straight chain number limiting parameter M.

The above-described example is visualized as in FIG. 26. Although the maximum space is identical, excess space is created and it can be understood that the 6$^{th}$ or 7$^{th}$ amino acid residue can be made the smaller space in reality.

Therefore, the straight chain limiting parameter M is added and a space parameter s(x) using the straight chain number limiting parameter s(x). As a result, the space can be limited as follows, and the number of bits can be suppressed without lowering accuracy.

$$V_i = \bigcup_{r \in J} S_r$$

$$i = \{1, 2, 3, \ldots n\}$$

$$s(x) = \left\lfloor \frac{x-1}{M} \right\rfloor \times (M-2) + ((x-1) \bmod N) + 1$$

When the space limiting parameter L is an even number, and i<L:
 J={s(1), s(3), . . . S(i)} in case of an odd numbered (i=odd number) amino acid residue.
 J={s(2), s(4), . . . S(i)} in case of an even numbered (i=even number) amino acid residue.

When the space limiting parameter L is an even number, and i>L:
 J={s(2), s(4), . . . S(L−1)} in case of an odd numbered (i=odd number) amino acid residue.
 J={s(2), s(4), . . . S(L)} in case of an even numbered (i=even number) amino acid residue.

When the space limiting parameter L is an odd number, and i<L:
 J={s(1), s(3), . . . S(i)} in case of an odd numbered (i=odd number) amino acid residue.
 J={s(2), s(4), . . . S(i)} in case of an even numbered (i=even number) amino acid residue.

When the space limiting parameter L is an odd number, and i>L:
 J={s(2), s(4), . . . S(L)} in case of an odd numbered (i=odd number) amino acid residue.
 J={s(2), s(4), . . . S(L−1)}} in case of an even numbered (i=even number) amino acid residue.

Figure 27:
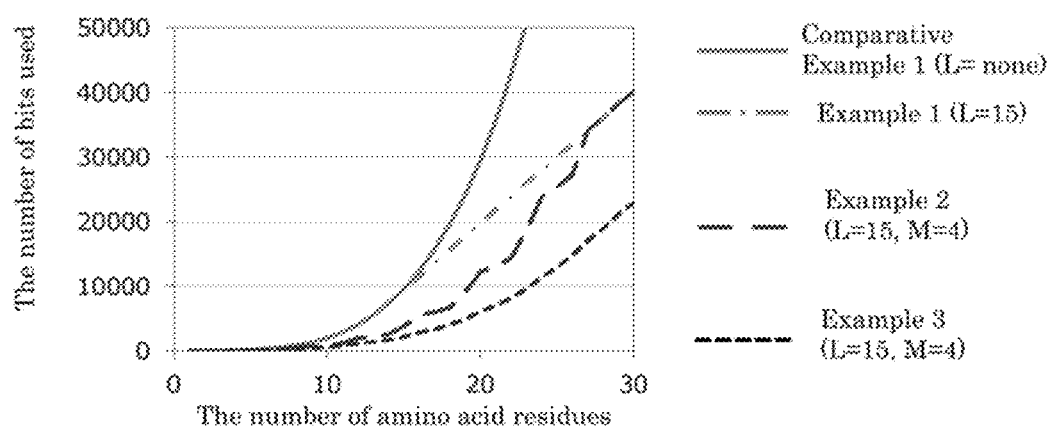
FIG. 27 is a graph depicting comparison of the number of bits used.

In the descriptions above, the disclosed technology described with reference to FIGS. 5 and 6 is determined as Example 1, the disclosed technology described with reference to FIGS. 20 and 21 is determined as Example 2, and the disclosed technology described with reference to FIGS. 24 and 25 is determined as Example 3. In each Examples, a change of the number of bits used when the parameter is determined as follows is illustrated in FIG. 27.

Example 1: L=15
Example 2: L=15, M=5
Example 3: L=15, M=5
Comparative Example 1: No restriction It was confirmed in all of Examples that the number of bits used could be significantly reduced compared to Comparative Example 1 where no restriction was given, and a compound having relatively a large scale of a problem (e.g., a protein) could be used as a target of a search.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A device for searching for a drug in which amino acid residues are linked with one another, comprising:
 a computer programmed to
  define, based on a number k, from 10 to 30, of the plurality of amino acid residues, a lattice space that is a collection of lattices where the plurality of amino acid residues are sequentially arranged,
  generate a limited lattice space where any of the amino acid residues is arranged in any of the lattices of the lattice space, followed by arranging a next amino acid residue to be linked next in the lattice space, the limited lattice space created by eliminating, from the lattice space, undesirable regions for the next amino acid residue to be arranged based on a space limiting parameter L, where L<k, assign a bit expressing presence of an amino acid residue in a position as 1 and absence of the amino acid residue as 0 to each of lattice points, to which each of the amino acid residues can be arranged, in the limited lattice space, and obtain an Ising model of the drug, by setting an $H_{one}$ restriction of only one of each first to n-numbered amino acids, an $H_{conn}$ restriction that the first to n-numbered amino acids are all linked with one another, an $H_{olap}$ restriction that the first to n-numbered amino acids are not overlapped with one another, and an $H_{pair}$ restriction representing an interaction between amino acids, calculating an entire energy E(x) of the compound based on $E(x)=H=H_{one}+H_{conn}+H_{olap}+H_{pair}$, and converting the entire energy to an energy formula of the Ising model; and an annealing machine configured to perform a ground state search on the Ising model obtained through conversion based on restriction conditions related to each of the lattice points according to simulated annealing, to thereby calculate minimum energy of the Ising model.

2. The device according to claim 1, wherein the generation of the limited lattice space is performed by setting a maximum number (M) of the compound groups arranged in a straight chain, where M<n.

3. The device according to claim 1, wherein generation of the limited lattice space is performed by setting the maximum number (M) of the compound groups arranged in a straight chain, where M<n, and excluding excess lattices present in a lattice space generated by setting the maximum number.

4. A method for searching a drug in which amino acid residues are linked with one another, the method comprising:

defining, based on a number k, from 10 to 30, of the plurality of amino acid residues, a lattice space that is a collection of lattices where the plurality of amino acid residues are sequentially arranged;

generating a limited lattice space where any of the amino acid residues is arranged in any of the lattices of the lattice space, followed by arranging a next amino acid residue to be linked next in the lattice space, the limited lattice space created by eliminating, from the lattice space, undesirable regions for the next amino acid residue to be arranged based on a space limiting parameter L, where L<k;

assigning a bit expressing presence of an amino acid residue in a position as 1 and absence of the amino acid residue as 0 to each of lattice points, to which each of the amino acid residues can be arranged, in the limited lattice space;

obtaining an Ising model of the drug, by setting an $H_{one}$ restriction of only one of each first to n-numbered amino acids, an $H_{conn}$ restriction that the first to n-numbered amino acids are all linked with one another, an $H_{olap}$ restriction that the first to n-numbered amino acids are not overlapped with one another, and an $H_{pair}$ restriction representing an interaction between amino acids, calculating an entire energy of the compound E(x) based on $E(x)=H=H_{one}+H_{conn}+H_{olap}+H_{pair}$, and converting the entire energy E(x) to the energy formula of the Ising model; and performing by an annealing machine a ground state search on the Ising model obtained through conversion based on restriction conditions related to each of the lattice points according to simulated annealing, to thereby calculate minimum energy of the Ising model.

5. The method according to claim 4, wherein the generating the limited lattice space is performed by setting the maximum number of compound groups arranged in a straight chain.

6. The method according to claim 4, wherein the generating the limited lattice space is performed by setting the maximum number (M) of the compound groups arranged in a straight chain, where M<n, and excluding excess lattices present in a lattice space generated by setting the maximum number.

7. A device for searching for a drug in which amino acid residues are linked with one another, comprising:

a computer programmed to define, based on a number k, from 10 to 30, of the plurality of amino acid residues, a lattice space that is a collection of lattices where the plurality of amino acid residues are sequentially arranged and $$V_i = \bigcup_{r \in J} S_r,$$

where a lattice space Vi is a collection of lattice points Sr with a radius r in which the plurality of amino acid residues are sequentially arranged, n is an integer from 10 to 30, i={1, 2, 3, ... n}, in case of an odd numbered (i=odd number) amino acid residue, J={1, 3, ... i}, and in case of an even numbered (i=even number) amino acid residue J={2, 4, ... i}, generate a limited lattice space where any of the amino acid residues is arranged in any of the lattices of the lattice space, followed by arranging a next amino acid residue to be linked next in the lattice space, the limited lattice space created by eliminating, from the lattice space, undesirable regions for the next amino acid residue to be arranged based on a space limiting parameter L, where L<k and, $$V_i = \bigcup_{r \in J} S_r$$

where i={1, 2, 3, ... n}, when the space limiting parameter L is an even number, and i<L:

J={1, 3, ... i} in case of an odd numbered (i=odd number) amino acid residue and J={2, 4, ... i} in case of an even numbered (i=even number) amino acid residue, when the space limiting parameter L is an even number and i>L:

J={1, 3, ... L–} in case of an odd numbered (i=odd number) amino acid residue and J={2, 4, ... L} in case of an even numbered (i=even number) amino acid residue, when the space limiting parameter L is an odd number and i<L:

J={1, 3, ... i} in case of an odd numbered (i=odd number) amino acid residue and J={2, 4, . . . i} in case of an even numbered (i=even number) amino acid residue, and when the space limiting parameter L is an odd number and i>L:

J={1, 3, . . . L} in case of an odd numbered (i=odd number) amino acid residue and J={2, 4, . . . L−1} in case of an even numbered (i=even number) amino acid residue, assign a bit expressing presence of an amino acid residue in a position as 1 and absence of the amino acid residue as 0 to each of lattice points, to which each of the amino acid residues can be arranged, in the limited lattice space, and obtain an Ising model of the drug, by setting an $H_{one}$ restriction of only one of each first to n-numbered amino acids, an $H_{conn}$ restriction that the first to n-numbered amino acids are all linked with one another, an $H_{olap}$ restriction that the first to n-numbered amino acids are not overlapped with one another, and an $H_{pair}$ restriction representing an interaction between amino acids, calculating an entire energy $E(x)$ of the compound based on $E(x)=H=H_{one}+H_{conn}+H_{olap}+H_{pair}$, and converting the entire energy to an energy formula of the Ising model expressed by $$E(x) = -\sum_{\langle i,j \rangle} W_{ij} x_i x_j - \sum_i b_i x_i$$

where states $x_i$ and $x_j$ may be 0 or 1, 0 representing absence and 1 representing presence, $W_{ij}$ is a weighting coefficient in an integration of a product of two neuron circuit states for all selectable combinations of two neuron circuits from all neuron circuits without any omission or overlap, and $b_i$ is a bias value and $x_i$ is a state of each of the neuron circuits, respectively; and an annealing machine configured to perform a ground state search on the Ising model obtained through conversion based on restriction conditions related to each of the lattice points according to simulated annealing, to thereby calculate minimum energy of the Ising model.

* * * * *